United States Patent [19]

Ueda et al.

[11] Patent Number: 4,472,433
[45] Date of Patent: Sep. 18, 1984

[54] PHENOXYPHENYL ACETIC ACIDS AND THEIR MEDICINAL USE

[75] Inventors: Ikuo Ueda, Toyonaka; Yoshihiko Kitaura, Suita; Nobukiyo Konishi, Mukou, all of Japan

[73] Assignee: Fujisawa Pharmaceutical Co., Ltd., Osaka, Japan

[21] Appl. No.: 291,498

[22] Filed: Aug. 10, 1981

Related U.S. Application Data

[63] Continuation of Ser. No. 063,088, Aug. 2, 1979, abandoned.

[30] Foreign Application Priority Data

Aug. 8, 1978 [GB] United Kingdom ............... 32609/78

[51] Int. Cl.$^3$ ................. C07C 101/72; A61K 31/195
[52] U.S. Cl. .................................. 424/319; 562/452; 560/45
[58] Field of Search ............. 562/452; 424/319; 71/116; 560/45

[56] References Cited

U.S. PATENT DOCUMENTS

3,981,905  9/1976  Adams et al. ...................... 562/452

FOREIGN PATENT DOCUMENTS

1072998  1/1960  Fed. Rep. of Germany ...... 562/452

OTHER PUBLICATIONS

Louden et al., *Journal Chem. Soc.*, 1957, 3809–13.
Sindelar et al., *Collection Czechoslov. Chem. Commun.*, Journal 40, pp. 2649–2666 (1975).

*Primary Examiner*—Henry R. Jiles
*Assistant Examiner*—Robert C. Whittenbaugh
*Attorney, Agent, or Firm*—Oblon, Fisher, Spivak, McClelland & Maier

[57] ABSTRACT

A compound of the formula:

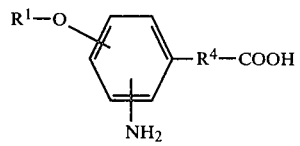

wherein $R^1$ is phenyl substituted with halogen or lower alkyl, and $R^4$ is a group of the formula $C_nH_{2n}$ in which n is an integer of 1 to 7; or a pharmaceutically acceptable salt thereof. The compound exhibits antipyretic, analgesic and anti-inflammatory properties.

2 Claims, No Drawings

PHENOXYPHENYL ACETIC ACIDS AND THEIR MEDICINAL USE

This is a continuation, of application Ser. No. 063,088, filed Aug. 2, 1979, now abandoned.

This invention relates to new phenyl alkanoic acid, its derivative at the carboxy group, and pharmaceutically acceptable salt thereof, which have antiinflammatory, analgesic and antipyretic activities, and an intermediate for preparing the same, to processes for preparation thereof and to pharmaceutical composition comprising the same.

The phenyl-alkanoic acid of this invention can be represented by the formula:

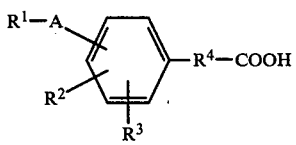

[I]

wherein
 $R^1$ is aryl, ar(lower)alkyl or pyridyl, each of which may be substituted with halogen, amino, lower alkyl, lower alkoxy or carboxy(lower)alkyl,
 $R^2$ is hydrogen or halogen,
 $R^3$ is amino, lower alkylamino, acylamino or nitro,
 $R^4$ is a group of the formula $C_nH_{2n}$ in which n is an integer of 1 to 7, and
 A is oxy, thio, sulfinyl, sulfonyl or imino.

In this specification, it is to be understood that the term "lower" used in connection with an alkyl and alkoxy group is intended to mean a group having up to seven carbon atoms.

With regard to the groups as defined in the above, the more detailed explanation will be made and preferred examples thereof will be illustrated in the following.

The "aryl" group and the "aryl" moiety of the ar(-lower)alkyl group may be an aromatic hydrocarbon residue and preferably may include phenyl, naphthyl, tolyl, xylyl, mesityl, cumenyl and the like.

The "lower alkyl" group and the "lower alkyl" moiety of the ar(lower)alkyl, carboxy(lower)alkyl and lower alkylamino group may include the straight and branched one such as methyl, ethyl, propyl, isopropyl, butyl, isobutyl, t-butyl, pentyl, hexyl or the like, in which the $C_{1-4}$ alkyl is preferable, and the $C_{1-2}$ alkyl is more preferable.

The "halogen" may include fluorine, chlorine, bromine and iodine.

The "lower alkoxy" group may be the straight or branched one such as methoxy, ethoxy, propoxy, isopropoxy, butoxy, isobutoxy, t-butoxy, pentyloxy, hexyloxy or the like, in which the $C_{1-4}$ alkoxy is preferable, and the $C_{1-2}$ alkoxy is more preferable.

The lower alkylamino group may include both of mono(lower)alkylamino group and di(lower)alkylamino group and the lower alkyl moiety thereof is to be referred to the above exemplification.

The "acyl" moiety of the acylamino group may be a residue of a carboxylic acid or sulfonic acid and preferably may include lower alkanoyl (e.g. formyl, acetyl, propionyl, butyryl, isopropionyl, isobutyryl, pentanoyl, hexanoyl, etc.); lower alkanesulfonyl (e.g. mesyl, ethanesulfonyl, propanesulfonyl, butanesulfonyl, etc.) and the like, in which the preferred alkane moiety is $C_{1-4}$, and the more preferred one is $C_{1-2}$.

The group of the formula: $C_nH_{2n}$ for $R^4$ may be lower alkylene and lower alkylidene such as methylene, ethylene, ethylidene, propylidene, butylidene, isopropylidene, propylene, trimethylene, tetramethylene, pentamethylene, hexamethylene or the like, preferably lower alkylidene, and the most preferably methylene.

The "derivative at the carboxy group" of the compound [I] includes an ester, an amide and a nitrile.

The suitable "ester" may be a lower alkyl ester, in which the lower alkyl moiety may be the same as those exemplified above, preferably $C_{1-4}$ alkyl and more preferably $C_{1-3}$ alkyl.

The suitable "amide" may be an amide, N-lower alkyl amide, N,N-di(lower)alkylamide in which the lower alkyl moiety may be substituted with hydroxy group(s) and an intramolecular amide of the formula:

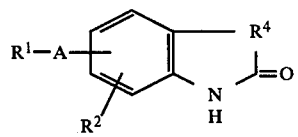

wherein $R^1$, $R^2$, $R^4$ and A are each as defined above, which can be formed by intramolecular amidation of the amino group for $R^3$ and the carboxy group.

In case that the amide is an N,N-di(lower)alkyl amide, these lower ($C_{1-3}$) alkyl moieties can be linked together, directly or with interruption by nitrogen atom, to form a N-heterocyclic group such as pyrrolidinyl, piperidino, piperazinyl, 4-methylpiperadinyl, 4-hydroxyethylpiperadinyl or the like.

The "pharmaceutically acceptable salt" of the object compound [I] may be a conventional one and may include a salt with an inorganic base or acid, for example, a metal salt such as an alkali metal salt (e.g. sodium salt, potassium salt, etc.), an alkaline earth metal salt (e.g. calcium salt, magnesium salt, etc.), ammonium salt, an inorganic acid salt (e.g. hydrochloride, hydrobromide, sulfate, phosphate, carbonate, bicarbonate, etc.), a salt with an organic base or acid, for example, an amine salt (e.g. trimethylamine salt, triethylamine salt, pyridine salt, procaine salt, picoline salt, dicyclohexylamine salt, N,N'-dibenzylethylenediamine salt, N-methylglucamine salt, diethanolamine salt, triethanolamine salt, tris(hydroxymethylamino)methane salt, phenethylbenzylamine salt, etc.), a carboxylic or sulfonic acid salt (e.g. acetate, maleate, lactate, tartrate, mesylate, benzenesulfonate, tosylate, etc.), a basic or acidic amino acid salt (e.g. arginine salt, aspartic acid salt, glutamic acid salt, lysine salt, serine salt, etc.), and the like.

The object compound [I] of this invention and the intermediate for preparing the same can be prepared as illustrated below.

Process A

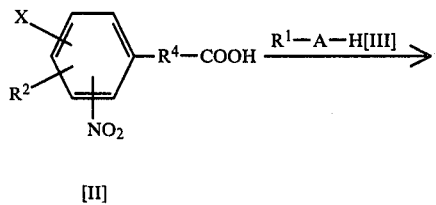

[II]

-continued
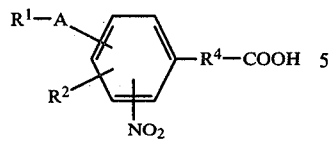
[Ia]
Process B
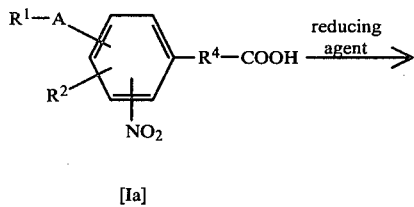
[Ia]
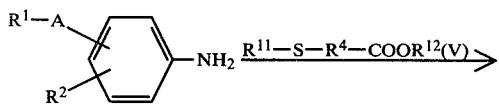
[Ib]
Process C
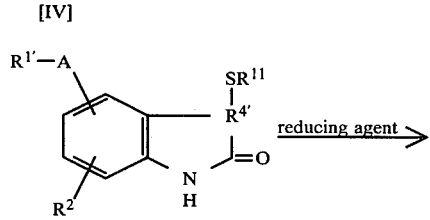
[IV]
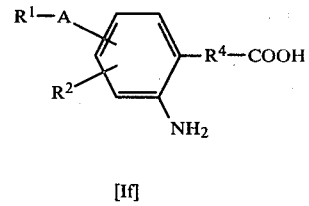
[VI]
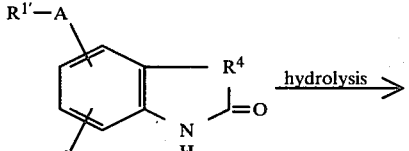
[Ic']
Process D
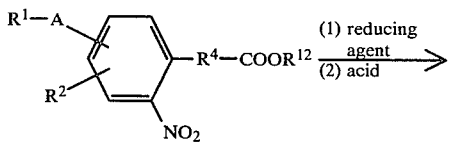
[Id']
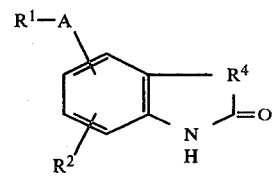
[Id]
Process E
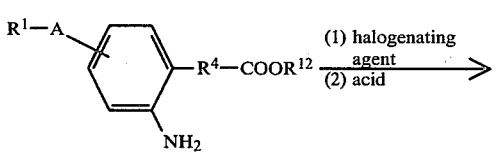
[Ie']
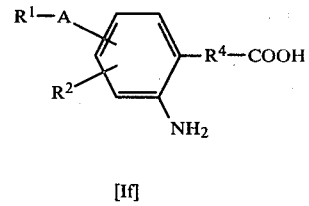
[Ie]
Process F
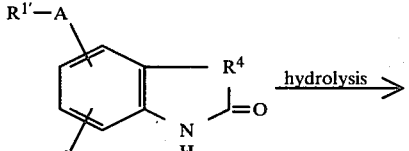
[Ic']
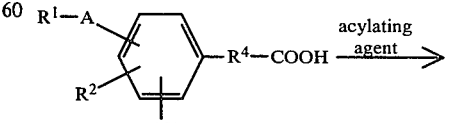
[If]
Process G
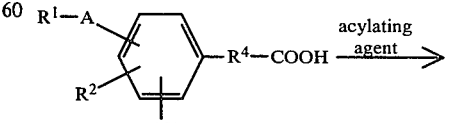
[Ib]

-continued

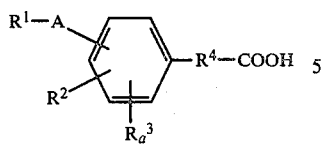

[Ig]

Process H

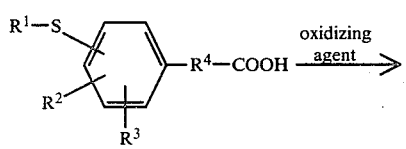

[Ih']

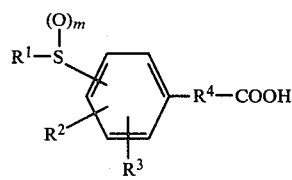

[Ih]

Process I

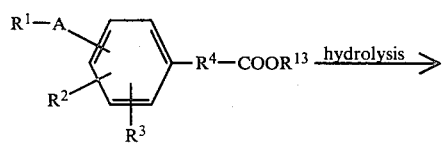

[Ii']

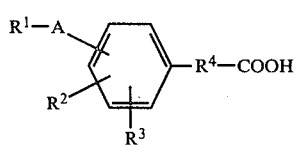

[Ii]

Process J

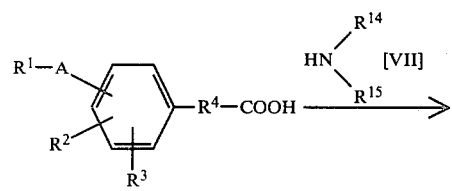

[Ij']

-continued

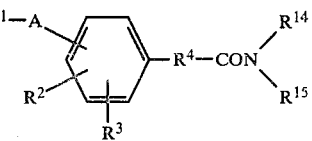

[Ij]

Process K

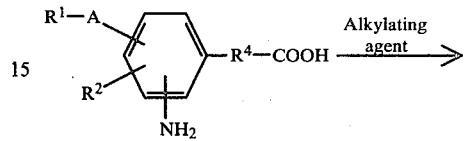

[Ib]

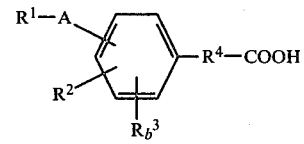

[Ik]

wherein
R$^1$, R$^2$, R$^3$, R$^4$ and A are each as defined above,
R$^{1'}$ is aryl, ar(lower)alkyl or pyridyl, each of which may be substituted with halogen, amino, lower alkyl or lower alkoxy, or a group of the formula:

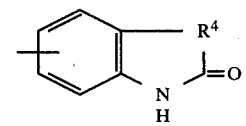

R$_a^2$ is halogen,
R$_a^3$ is an acylamino,
R$_b^3$ is a lower alkylamino,
R$^{4'}$ is a group of the formula: C$_n$H$_{2n-1}$ in which n is as defined above,
R$^{11}$ is lower alkyl,
R$^{12}$ is hydrogen or lower alkyl,
R$^{13}$ is lower alkyl,
R$^{14}$ and R$^{15}$ are each hydrogen or lower alkyl which may be substituted with hydroxy group(s), and the lower alkyl groups for R$^{14}$ and R$^{15}$ may be linked together, directly or with interruption by nitrogen atom to form a N-containing heterocyclic group,
X is halogen, and
m is 1 or 2.

The "lower alkyl" for R$^{11}$, R$^{12}$, R$^{13}$, R$^{14}$ and R$^{15}$ may be the same as those illustrated before.

The "halogen" for X may be chlorine, bromine or iodine.

The processes as schematically shown in the above are explained in details in the following.

Process A

The compound [Ia], its derivative at the carboxy group and a salt thereof can be prepared by reacting a halo-phenyl compound [II], its derivative at the carboxy group or a salt thereof with a compound [III] in the presence of a condensing agent such as a metalic agent (e.g. cupric oxid, copper powder etc.) or the like.

The reaction is preferably conducted in the presence of a base such as sodium carbonate, potassium carbonate or the like.

This reaction may be conducted with or without a solvent and preferably under heating. Preferable solvent is the one having higher boiling point such as toluene, xylene, nitrobenzene, N,N-dimethylformamide or the like.

Process B

The compound [Ib], its derivative at the carboxy group and a salt thereof can be prepared by reacting a compound [Ia], its derivative at the carboxy group or a salt thereof with a reducing agent.

The reducing agent includes a conventional one which can be applied for reducing nitro group to amino group, preferred examples of which may be a metal (e.g. iron, tin, etc.) or a metal salt (e.g. iron chloride, cobalt chloride, etc.).

This reduction is usually conducted under-heating in a solvent such as water, a protic solvent such as alcohol (e.g. methanol, ethanol, etc.), or a mixture thereof. When a metal is used as a reducing agent, the reaction is preferably conducted in the presence of a base such as an ammonium salt (e.g. ammonium chloride, etc.) or the like.

Process C

The compound [Ic'] and its salt can be prepared by reacting an aniline compound [IV] with a sulfide compound [V] and then reducing at the resultant product [VI].

The reaction of a compound [IV] with a compound [V] is usually conducted in a solvent such as methylene chloride, chloroform or the like, and preferably under milder condition, for instance, under cooling at about −40° to −60° C.

The reduction of the resultant compound [VI] is conducted by using a conventional reductive catalyst. Preferred examples of which may be Raney nickel. The reaction is usually conducted in a solvent such as dioxane, methanol, ethanol or any other conventional solvent which does not adversely influence the reaction or a mixture thereof.

When the starting compound [IV] has 2-aminophenyl group for $R^1$, a bis-compound [VI] and [Ic'] may be occasionally obtained in this process, and these cases are to be included within the scope of this process.

Process D

The compound [Id] and its salt can be prepared by reducing a nitrophenyl compound [Id'] and then treating the resultant product with an acid. Suitable acid includes an inorganic acid such as hydrochloric acid, sulfuric acid, an organic acid such as p-toluenesulfonic acid, and the like. The reduction of the first step can usually be conducted substantially in the same manner as that of the Process B, and the acid treatment of the second step is usually carried out at ambient temperature or under heating.

This process can preferably be conducted by reducing the starting compound [Id'] in the presence of an acid to produce the product [Id] directly, and this case is to be included within the scope of this process.

Process E

The compound [Ie] can be prepared by reacting a compound [Ie'] with a halogenating agent and then treating the resultant product with an acid substantially in the same manner as the above Process D.

The halogenating agent includes a conventional agent which can halogenate a benzene ring, and preferably may be chlorine, bromine, N-chlorosuccinimide, N-bromosuccimide, N-chlorophthalimide or the like. The halogenation reaction is usually conducted under heating in a conventional solvent which does not adversely affect this reaction such as dioxane, chloroform, dichloroethane, benzene or the like.

Process F

The compound [If] and its salt can be prepared by hydrolyzing a compound [Ic'] or its salt.

This reaction may preferably be conducted by using a rather strong base such as a caustic alkali (e.g. sodium hydroxide, potassium hydroxide, etc.) or the like, in a solvent such as water, a conventional organic solvent, (e.g. dioxane, tetrahydrofuran, ethyleneglycol, etc.) or a mixture thereof under heating. When a bis-compound [Ic'] where $R^{1'}$ is a group of the formula:

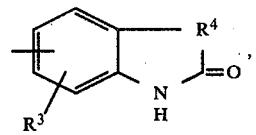

is used as a starting material, the bis-compound [If] where $R^1$ is a group of the formula:

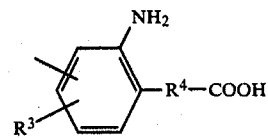

can be prepared in this process, and this case is also included within the scope of this process.

Process G

The compound [Ig], its derivative at the carboxy group and a salt thereof can be prepared by reacting a compound [Ib], its derivative at the carboxy group or a salt thereof with an acylating agent.

The acylating agent includes a lower alkanoic acid, lower alkanesulfonic acid and reactive derivatives thereof. The reactive derivative of the acid includes a conventional one such as acid halide, acid anhydride, acid azide, activated ester, activated amide, and the like. In case that the acid is used in a form of the free acid, the reaction is preferably conducted in the presence of a conventional condensing agent such as N,N'-dicyclohexylcarbodiimide, alkoxyacetylene, trialkyl phosphite, phosphorus oxychloride or the like.

The reaction is usually conducted in a solvent such as methylene chloride, acetone, dioxane, tetrahydrofuran or any other solvent which does not adversely influence the reaction, under cooling or at ambient temperature, and preferably in the presence of a conventional inorganic or organic base such as an alkali metal bicarbonate, tri(lower)alkylamine, pyridine, N-(lower)alkylmorphorine or the like.

Process H

The compound [Ih], its derivative at the carboxy group and a salt thereof can be prepared by reacting a compound [Ih'], its derivative at the carboxy group or a salt thereof with an oxidizing agent.

The oxidizing agent includes a conventional one which can oxidize a thio group into sulfinyl or sulfonyl group, and preferably may be m-chloroperbenzoic acid, perbenzoic acid, hydrogen peroxide or the like.

This reaction is usually conducted in a conventional solvent such as chloroform, methylenechloride or the like.

Process I

The free carboxylic acid [Ii] and its salt can be prepared by subjecting an ester compound [Ii'] or its salt to hydrolysis.

The method of this reaction includes a conventional hydrolysis and preferably may be carried out in the presence of a rather strong base (e.g. sodium hydroxide, potassium hydroxide, etc.) in a solvent such as water, an organic solvent (e.g. methanol, ethanol, ethyleneglycol or any other conventional one which does not adversely influence the reaction) or an optional mixture thereof, at ambient temperature or under heating.

It is to be noted that an intramolecular amide, i.e. a lactam as illustrated above, is occasionally isolated as a reaction product when a compound [Ii'] having an imino group in ortho position is used as a starting material and an acid (e.g. hydrochloric acid, sulfuric acid, etc.) is used in the post-treatment of this process and such case is also included in this process.

Process J

The compound [Ij] and its salt can be prepared by reacting a compound [Ij'], its reactive derivative at the carboxy group or a salt thereof with an amine [VII].

This reaction may be conducted in substantially the same manner as the aforementioned Process G.

Process K

The compound [Ik], its derivative at the carboxy group and a salt thereof can be prepared by reacting a compound [Ib], its derivative at the carboxy group or a salt thereof with an alkylating agent.

The alkylating agent may be a conventional N-alkylating agent such as alkyl halide (e.g. methyl iodide, ethyl iodide, etc.), dialkyl sulfate (e.g. dimethyl sulfate, diethyl sulfate etc.) or the like. This reaction is usually conducted in a conventional solvent such as dimethylformamide, benzene, toluene or the like, at ambient temperature or under warming, and preferably in the presence of a base such as sodium carbonate, potassium carbonate or the like.

All the compounds produced by the above processes can be isolated from the reaction mixture and purified by a conventional method. And, in case that the object product having a free amino and/or carboxy group is obtained as the reaction product in these processes, it may also be transformed into an optional salt thereof as illustrated above by a conventional salt formation method.

It can be understood through the following pharmacological test data that the object compound (I) of the present invention exhibits antiinflammatory, analgesic and antipyretic activities and is useful as an antiinflammatory, analgesic and antipyretic agent for human beings and animals.

Test method (1)

Ten male 5 week old Hartley rats, each weighing about 350 g. were used per group. The backs of each animal were depilated 24 hours before the test. An adhesive tape with 3 small holes of 9 mm. diameter was placed on the depilated skin and then the animal was exposed to ultra-violet radiation from an ultra-violet lamp (500 W, manufactured by Engelhard Hanovia Inc.) at a distance of 13 cm. for 80 seconds. Two hours later, the degree of erythema was estimated on the basis of the following scores:

1.0: erythema with clear border,
0.5: erythema with unclear border,
0.0: scarcely erythema.

The drugs were regarded as being effective when the total of 3 points was below 1.5.

Each dosage of the test compound was administered orally in a suspension form in 20 ml. of 0.5% methyl cellosolve aqueous solution. Half of the test sample was administered one hour before the radiation and the remaining half of the test solution was administered just after radiation. The test results obtained are given in the following Table 1:

TABLE 1

| Test compound obtained in | Number of rats estimated as effective | |
|---|---|---|
| | 2 mg/kg | 10 mg/kg |
| Example 2 - (2) | 9 | 10 |
| Example 5 - (2) | 8 | 10 |
| Example 10 - (2) | 5 | 10 |

Test method (2)

The stomach was removed from Sprague-Dawley rats, weighing about 180 g., after the animals were fasted overnight. A strip of stomach fundus was suspended under initial tension of 0.6 g. in a 10 ml. organ bath containing Tyrode solution. Arachidonic acid ($1.0 \times 10^{-5}$ g./ml.) was employed as the spasmogen. Several doses of the test compound were added to the individual bath fluid 15 minutes before the addition of arachidonic acid. The value of contraction induced by arachidonic acid was measured and plotted dose-activity curve. $ED_{50}$ value of each test compound was obtained by interpolation from the dose-activity curve. The results obtained are given in the following Table 2.:

TABLE 2

| Test compound obtained in | $ED_{50}$ (g./ml.) |
|---|---|
| Example 2 - (2) | $1.6 \times 10^{-6}$ |
| Example 4 - (2) | $1.7 \times 10^{-6}$ |
| Example 5 - (2) | $1.3 \times 10^{-6}$ |
| Example 7 - (2) | $0.16 \times 10^{-6}$ |
| Example 10 - (2) | $2.5 \times 10^{-6}$ |
| Example 19 | $2.4 \times 10^{-6}$ |

Test method (3)

Male ddy strain mice, weighing 24.0–32.0 g, were used. Each dose group consisted of 10 animals. Writhing syndrome was produced by an intraperitoneal injection of 20 ml/kg of 0.6% acetic acid. Each animals was observed for writhing syndrome from 3 to 13 minutes after acetic acid. The drug were given orally 60 minutes before acetic acid. The frequency of writhing syndrome for 10 minutes in the treated animals was compared with that in the control. Control animals received the vehicle.

The test substances, the compound obtained in the Example 5-(2) was suspended in 0.5% methylcellulose.

$ED_{50}$ value was calculated according to the Litchfield-Wilcoxon's method with a computer program.

The test substance, given orally, had dose-related inhibiting effects on the writhing syndrome caused by acetic acid.

The $ED_{50}$ value of the test compound was 19.6 mg/kg.

Test method (4)

Male SD strain rats aged 6 weeks, weighing 164–235 g, were divided into 4 groups i.e. A, B, A' and B' of 10 animals each and were treated as shown below:

|  | Pretreated with | Treated with |
|---|---|---|
| Group A | saline | 0.5% methylcellulose |
| Group B | 5% Brewer's yeast | 0.5% MC |
| Group A' | saline | Test substance |
| Group B' | 5% Brewer's yeast | Test substance |

The test substance or 0.5%MC were given orally to rats 4 hr after subcutaneous injection of 5% Brewer's yeast or saline. The rectal temperature was measured with a thermister probe inserted about 4.5–5.0 cm into the rectum 4 hr before, and 1 and 2 hr after the injection of test substance.

The antipyretic effect (%) of test substance on the Brewer's yeast-induced hyperthermia at 1 and 2 hr after the injection of test substance was calculated from the mean rectal temperature (rectal temp.) in each group by the following formula:

$$\text{Antipyretic effect (\%)} = \left(1 - \frac{\text{Rectal temp. of group B'} - \text{Rectal temp. of group A'}}{\text{Rectal temp. of group B} - \text{Rectal temp. of group A}}\right) \times 100$$

All experiments were performed at an ambient temperature of 22.0°–22.5° C.

Test substance, the compound obtained in the Example 5-(2) was dissolved in 0.5%MC at a dose of 10 mg/kg and 100 mg/kg, and also suspended in 0.5%MC at a dose of 320 mg/kg, and Brewer's yeast was suspended in saline.

Statistics: Calculation of $ED_{50}$ value according to the Litchfield-Wilcoxon's method was performed with a computer program. Statistic analysis of difference between the control and treated groups according to the Student's t-test or Cochran-Cox test was performed with a computer program.

In the saline-treated rats, test substance, at a dose of 10 mg/kg, produced a rise but, at a dose of 320 mg/kg, produced a fall of the rectal temperature at 1 hr after injection, although both changes were slight but significant. At 2 hr after injection, test substance, at doses of 100 mg/kg and 320 mg/kg, produced a significant fall of the rectal temperature. In the Brewer's yeast-treated rats, test substance showed the antipyretic effect on the Brewer's yeast-induced hyperthermia at all doses 1 and 2 hr after injection. $ED_{50}$ values at 1 and 2 hr after injection were 37.3 mg/kg and 12.8 mg/kg, respectively.

As being apparent from the above test results, the object compounds (I) of the present invention are useful for the antiinflammatory, analgesic and antipyretic medicines.

The effective ingredient may usually be administered with a dose of 10 to 500 mg., 1 to 4 times a day in a preparations such as tablet, granule, powder, capsule, syrup, injection, suppository and the like. However, the above dosage may be increased or decreased according to the age, weight or conditions of the patient or the administering method. The above mentioned preparations can be prepared in a conventional manner by using conventional carriers and additives.

The following examples are given for illustrating the present invention in more detail.

Preparation 1

Preparation of 2-(2-nitro-3-phenoxyphenyl)acetic acid and its ethyl ester

A mixture of ethyl 2-(2-nitro-3-chlorophenyl)acetate (15 g.), phenol (6.4 g.), anhydrous potassium carbonate (13 g.) and cupric oxide (4.5 g.) was stirred for 4 hours at 120° C. To the reaction mixture was added water and the mixture was extracted with diethyl ether. The extract was washed with a diluted aqueous solution of potassium carbonate and water, dried over magnesium sulfate and then evaporated under reduced pressure. The oily residue was distilled under reduced pressure to give ethyl 2-(2-nitro-3-phenoxypheny)acetate (5.2 g.) bp 160°–183° C./0.4 mmHg.

I.R. (Nujol): 1740, 1270 cm$^{-1}$.

N.M.R. (CCl$_4$): δ(ppm) 1.21 (3H, t, J=8 Hz), 3.61 (2H, s), 4.10 (2H, q, J=8 Hz), 6.76–7.39 (8H, m).

On the other hand, aqueous solution remaining after extraction with diethyl ether was acidified with hydrochloric acid and extracted with diethyl ether. The extract was washed with water, dried over magnesium sulfate and evaporated to give 2-(2-nitro-3-phenoxypheny)acetic acid (1.3 g.). mp 133° to 140° C.

Preparation 2

Preparation of 2-[2-nitro-3-(2-fluorophenoxy)phenyl]acetic acid and its ethyl ester A mixture of ethyl 2-(2-nitro-3-chlorophenyl)acetate (10 g.), 2-fluorophenol (5.8 g.), anhydrous potassium carbonate (8.5 g.) and cupric oxide (1 g.) was stirred for 5 hours at 130° C. To the reaction mixture was added conc. hydrochloric acid and water, and the mixture was extracted with benzene. The extract was washed with water, dried over magnesium sulfate and then evaporated under reduced pressure to give oily 2-[2-nitro-3-(2-fluorophenoxy)phenyl]acetic acid.

I.R. (Nujol): 1710, 1530, 1370, 1290 cm$^{-1}$.

N.M.R. (DMSO-d$_6$): δ(ppm) 3.87 (2H, s), 6.90–7.80 (7H, m).

To the above product were added ethanol and a small amount of conc. sulfuric acid, and the mixture was refluxed under heating for 1 hour. The solvent was distilled off from the reaction mixture and to the residue was added water. The mixture was extracted with diethyl ether, and the extract was washed with 5% aqueous sodium hydroxide and water in turn, dried over magnesium sulfate and evaporated under reduced pressure. The residue was distilled under reduced pressure to give oil of ethyl 2-[2-nitro-3-(2-fluorophenoxy)phenyl]acetate (6.5 g.). bp 175° to 185° C./0.7 mmHg.

I.R. (Film): 1740, 1280 cm⁻¹.
N.M.R. (CCl₄): δ(ppm) 1.23 (3H, t, J=8 Hz), 3.61 (2H, s), 4.08 (2H, q, J=8 Hz), 6.55–7.55 (7H, m).

Preparation 3

Preparation of 2-[2-nitro-3-(4-chlorophenoxy)phenyl]acetic acid and its ethyl ester A mixture of ethyl 2-(2-nitro-3-chlorophenyl)acetate (10 g.), 4-chlorophenol (7.8 g.), anhydrous potassium carbonate (8.5 g.) and cupric oxide (3 g.) was treated in a similar manner to the above Preparations to give 2-[2-nitro-3-(4-chlorophenoxy)phenyl]acetic acid (6.9 g.). mp 167° to 170° C.

A mixture of the product (6.9 g.), ethanol (50 ml.) and conc. sulfuric acid (1 ml.) was refluxed under heating for 1.5 hours. The reaction mixture was evaporated and extracted with diethyl ether. The extract was washed with a saturated aqeuous solution of sodium bicarbonate and water, dried over magnesium sulfate and evaporated under reduced pressure to give oily ethyl 2-[2-nitro-3-(4-chlorophenoxy)phenyl]acetate (7.0 g.).

I.R. (Film): 1740, 1265 cm⁻¹.

Preparation 4

Preparation of ethyl 2-[2-nitro-3-(3-chlorophenoxy)phenyl]acetate

A mixture of ethyl 2-(2-nitro-3-chlorophenyl) acetate (10 g.), 3-chlorophenol (7.8 g.), anhydrous potassium carbonate (8.5 g.) and cpuric oxide (3 g.) was treated in a similar manner to the above Preparations to give oily ethyl 2-[2-nitro-3-(3-chlorophenoxy)phenyl]acetate (4.6 g.).

I.R. (Film): 1745, 1270 cm⁻¹.
N.M.R. (CCl₄): δ(ppm) 1.23 (3H, t, J=7 Hz), 3.62 (2H, s), 4.10 (2H, q, J=7 Hz), 6.68–7.50 (7H, m).

Preparation 5

Preparation of 2-[2-nitro-3-(2-chlorophenoxy)phenyl]acetic acid and its ethyl ester A mixture of ethyl 2-(2-nitro-3-chlorophenyl)acetate (15 g.), 2-chlorophenol (11.7 g.), anhydrous pottassium carbonate (12.8 g.) and cupric oxide (1.5 g.) was treated in a similar manner to the above Preparations to give 2-[2-nitro-3-(2-chlorophenoxy)phenyl]acetic acid (4.6 g.). mp 162° to 164° C. A mixture of thus obtained product, ethanol and a small amount of conc. sulfuric acid was treated in a similar manner to the above to give oily ethyl 2-[2-nitro-3-(2-chlorophenoxy)phenyl]acetate (5 g.).

I.R. (Film): 1740, 1270 cm⁻¹.
N.M.R. (CCl₄): δ(ppm) 1.31 (3H, t, J=7 Hz), 3.65 (2H, s), 4.10 (2H, q, J=7 Hz), 6.60–7.75 (7H, m).

Preparation 6

Preparation of ethyl 2-[2-nitro-3-(3,4-dichlorophenoxy)phenyl]acetate

A mixture of ethyl 2-(2-nitro-3-chlorophenyl)acetate (10 g.), 3,4-dichlorophenol (7.4 g.), anhydrous potassium carbonate (8.5 g.) and cupric oxide (1 g.) was treated in a similar manner to the above to give oil of the captioned compound (6.6 g.)

I.R. (Film): 1740, 1270 cm⁻¹.
N.M.R. (CCl₄): δ(ppm) 1.23 (3H, t, J=7 Hz), 3,70 (2H, s), 4.09 (2H, q, J=7 Hz), 6.82–7.50 (6H, m).

Preparation 7

Preparation of ethyl 2-[2-nitro-3-(3,5-dichlorophenoxy)phenyl]acetate

A mixture of ethyl 2-(2-nitro-3-chlorophenyl)acetate (10 g.), 3,5-dichlorophenol (7.4 g.), anhydrous potassium carbonate (8.5 g.) and cupric oxide (1 g.) was treated in a similar manner to the above to give oil of the captioned compound (7.6 g.).

I.R. (Film): 1745, 1270 cm⁻¹.
N.M.R. (CCl₄): δ(ppm) 1.20 (3H, t, J=7 Hz), 3.65 (2H, s), 4.12 (2H, q, J=7 Hz), 6.55–7.50 (6H, m).

Preparation 8

Preparation of 2-[2-nitro-3-(2,3-dichlorophenoxy)phenyl]acetic acid and its ethyl ester.

A mixture of ethyl 2-(2-nitro-3-chlorophenyl)acetate (10 g.), 2,3-dichlorophenol (7.4 g.), anhydrous potassium carbonate (8.5 g.) and cupric oxide (1 g.) was treated in a similar manner to the above to give 2-[2-nitro-3-(2,3-dichlorophenoxy)phenyl]acetic acid (4.1 g.). mp 178° to 183° C.

A mixture of thus obtained product, ethanol and a small amount of conc. sulfuric acid was treated in a similar manner to the above to give oil of ethyl 2-[2-nitro-3-(2,3-dichlorophenoxy)phenyl]acetate (4.3 g.).

I.R. (Nujol): 1745, 1270 cm⁻¹.
N.M.R. (CCl₄): δ(ppm) 1.27 (3H, t, J=7 Hz), 3.70 (2H, s), 4.15 (2H, q, J=7 Hz), 6.67–7.50 (6H, m).

Preparation 9

Preparation of 2-[2-nitro-3-(2,4-dichlorophenoxy)phenyl]acetic acid and its ethyl ester.

A mixture of ethyl 2-(2-nitro-3-chlorophenyl)acetate (10 g.), 2,4-dichlorophenol (7.4 g.), anhydrous potassium carbonate (8.6 g.) and cupric oxide (1 g.) was treated in a similar manner to the above to give 2-[2-nitro-3-(2,4-dichlorophenoxy)phenyl]acetic acid (2.4 g.).

A mixture of thus obtained product, ethanol and a small amount of conc. sulfuric acid was treated in a similar manner to the above to give ethyl 2-[2-nitro-3-(2,4-dichlorophenoxy)phenyl]acetate (3.95 g.).

I.R. (Film): 1740, 1270 cm⁻¹.
N.M.R. (CCl₄): δ(ppm) 1.27 (3H, t, J=7 Hz), 3.67 (2H, s), 4.15 (2H, q, J=7 Hz), 6.65–7.52 (6H, m).

Preparation 10

Preparation of ethyl 2-[2-nitro-3-(o-tolyloxy)phenyl]acetate

A mixture of o-cresol (4.9 g.), ethyl 2-(2-nitro-3-chlorophenyl)acetate (10.0 g.), potassium carbonate (8.5 g.) and cupric oxide (1 g.) was treated in a similar manner to the above to give the captioned compound (3.4 g.). bp 173° to 176° C./0.2 to 0.4 mmHg.

I.R. (Film): 1741, 1530 cm⁻¹.
N.M.R. (CCl₄-D₂O): (ppm) 1.30 (3H, t, J=7 Hz), 2.25 (3H, s), 3.63 (2H, s), 4.17 (2H, q, J=7 Hz), 6.57–7.57 (7H, m).

Preparation 11

Preparation of ethyl 2-[2-nitro-3-(3,4-dimethylphenoxy)phenyl]acetate

A mixture of ethyl 2-(2-nitro-3-chlorophenyl)acetate (10 g), 3,4-dimethylphenol (5.5 g.), anhydrous potassium carbonate (8.5 g.) and cupric oxide (1 g.) was treated in a similar manner to the above to give the captioned compound (3.65 g.). bp 190° to 196° C./0.8 mmHg.

I.R. (Film): 1745, 1270 cm⁻¹.

N.M.R. (CCl$_4$): δ(ppm) 1.25 (3H, t, J=7 Hz), 2.22 (6H, s), 3.60 (2H, s), 4.13 (2H, q, J=7 Hz), 6.65–7.40 (6H, m).

Preparation 12

Preparation of ethyl 2-(2-nitro-3-phenylthiophenyl)acetate

A mixture of ethyl 2-(2-nitro-3-chlorophenyl)acetate (8.4 g.), sodium benzenethiolate (4.6 g.), and dimethylformamide (50 ml.) was treated in a similar manner to the above to give yellow needles of the captioned compound (7.25 g.). mp 65° to 67° C.

I.R. (Nujol): 1740 cm$^{-1}$.

N.M.R. (CDCl$_3$): δ(ppm) 1.30 (3H, t, J=7 Hz), 3.77 (2H, s), 4.20 (2H, q, J=7 Hz), 6.70–7.60 (8H, m).

Preparation 13

Preparation of ethyl 2-[2-nitro-3-(4-chlorophenylthio)phenyl]acetate

To a solution of potassium hydroxide (2.5 g.) in methanol (30 ml.) was dissolved 4-chlorobenzenethiol (6.5 g.), and methanol was distilled off to give potassium 4-chlorobenzenethiolate. To this product were added ethyl 2-(2-nitro-3-chlorophenyl)acetate (10 g.) and dimethylformamide (50 ml.) and stirred for 1.5 hours at 100° C. The reaction mixture was poured into water (300 ml.) and extracted with diethyl ether. The extract was washed with water, dried over magnesium sulfate and then evaporated under reduced pressure. The residue was recrystallized from a mixture of benzene and n-hexane to give yellow needles of the captioned compound (9.9 g.). mp 77° to 79° C.

I.R. (Nujol): 1740 cm$^{-1}$.

N.M.R. (CDCl$_3$): δ(ppm) 1.24 (3H, t, J=8 Hz), 3.76 (2H, s), 4.15 (2H, q, J=8 Hz), 7.00–7.46 (7H, m).

Preparation 14

Preparation of ethyl 2-[2-nitro-3-(2-chlorophenylthio)phenyl]acetate

A mixture of 2-chlorobenzenethiol (8.0 g.), ethyl 2-(2-nitro-3-chlorophenyl)acetate (12.2 g.), anhydrous potassium carbonate (7.5 g.) and dry dimethylformamide (50 ml.) was stirred for an hour at 85° C. The reaction mixture was poured into water (300 ml.) and extracted with diethyl ether. The extract was washed with a saturated aqueous solution of sodium chloride, dried over magnesium sulfate and evaporated under reduced pressure. The oily residue was pulverized and recrystallized from methanol (20 ml.) to give the captioned compound (11.6 g.). mp 78° to 80° C.

I.R. (Nujol): 1730, 1195 cm$^{-1}$.

N.M.R. (DMSO-d$_6$): δ(ppm) 1.20 (3H, t, J=7 Hz), 3.93 (2H, s), 4.13 (2H, q, J=7 Hz), 7.00–7.83 (7H, m).

Preparation 15

(1) Preparation of 2-oxo-3-methylthio-7-phenoxyindoline

Chlorine gas (3.1 g.) was absorved into dried methylene chloride (70 ml.) under cooling. To the solution was added dropwise a solution of ethyl methylthioacetate (6.35 g.) in methylene chloride (10 ml.) over 30 minutes under stirring at 31 60° C. and stirred for 10 minutes at the same temperature. A solution of 2-phenoxyaniline (17.5 g.) in methylene chloride (10 ml.) was added dropwise to the mixture over 30 minutes at −65° C. and stirred at the same temperature for an hour. A solution of triethylamine (7.5 g.) in methylene chloride (10 ml.) was added dropwise over 15 minutes at −65° C. and stirred for 30 minutes at the same temperature. The reaction mixture was allowed to stand at ambient temperature, and water (40 ml.) was added and stirred for 10 minutes. The organic layer was separated, dried over magnesium sulfate and evaporated under reduced pressure. The oily residue was subjected to column chromatography on silica gel (400 g.) and eluted with a mixture of benzene and n-hexane (1:1), benzene and ethyl acetate successively. The ethyl acetate eluate was concentrated and the powdery residue was recrystallized from a mixture of benzene and n-hexane to give white needles of the captioned compound (6.25 g.). mp 149° to 150° C.

I.R. (Nujol): 3150, 1700 cm$^{-1}$.

N.M.R. (DMSO-d$_6$): (ppm) 2.05 (3H, s), 4.27 (1H, s), 6.80–7.51 (8H, m), 8.15 (1H, broad s).

(2) Preparation of 2-oxo-7-phenoxyindoline

A mixture of the above product (4 g.), Raney nickel (W-2 type) (4 g.) and dried ethanol (70 ml.) was refluxed under heating for an hour with stirring. The reaction mixture was allowed to stand at ambient temperature and the supernatant was separated by decantation. The residue was washed with ethanol (30 ml.), and the supernatant was separated by decantation. The supernatants were combined together, filtered and then evaporated under reduced pressure. The residue was washed with n-hexane and dried to give the captioned compound (2.85 g.). mp 135° to 146° C.

I.R. (Nujol): 3150, 1700 cm$^{-1}$.

N.M.R. (CDCl$_3$): δ(ppm) 3.50 (2H, s), 6.70–7.40 (8H, m), 7.65 (1H, broad s).

Preparation 16

(1) Preparation of 2-oxo-3-methyl-3-methylthio-7-(2-chlorophenoxy)indoline.

Chlorine gas (2.7 g.), ethyl 2-methylthiopropionate (5.6 g.), 2-(2-chlorophenoxy)aniline (16.5 g.), triethylamine (3.8 g.) and methylene chloride (60 ml.) were treated in a similar manner to that of the Preparation 15-(1) to give white powdery crystals of the captioned compound (6 g.). mp 144° to 145° C.

I.R. (Nujol): 3180, 3080, 1720 cm$^{-1}$.

N.M.R. (DMSO-d$_6$): δ(ppm) 1.55 (3H, s), 1.91 (3H, s), 6.67–7.64 (7H, m).

(2) Preparation of 2-oxo-3-methyl-7-(2-chlorophenoxy)indoline

A mixture of the above product (8 g.) Raney nickel (W-2 type)(15 ml.) and dioxane (100 ml.) was treated in a similar manner to that of the Preparation 15-(2) to give the captioned compound (6.5 g.). mp 138° to 139° C.

I.R. (Nujol): 3200, 1710 cm$^{-1}$.

N.M.R. (DMSO-d$_6$): δ(ppm) 1.36 (3H, d, J=8 Hz), 3.51 (1H, q, J=8 Hz), 6.55–7.70 (7H, m).

Preparation 17

(1) Preparation of 2-oxo-3-methylthio-7-(2,6-dichlorophenoxy)indoline

Chlorine gas (0.74 g.), ethyl methylthioacetate (1.4 g.), 2-(2,6-dichlorophenoxy)aniline (5.3 g.), triethylamine (1.65 g.) and methylene chloride (40 ml.) were treated in a similar manner to that of the Preparation 15-(1) to give the captioned compound (2.65 g.). mp>230° C.

I.R. (Nujol): 3150, 3080, 1720 cm$^{-1}$.

N.M.R. (DMSO-d$_6$): δ(ppm) 2.00 (3H, s), 4.64 (1H, s), 6.27–7.70 (6H, m).

(2) Preparation of 2-oxo-7-(2,6-dichlorophenoxy)indoline

A mixture of the above product (4.8 g.) Raney, nickel (W-2 type)(15 ml.) and dried ethanol (60 ml.) was refluxed under heating for an hour with stirring. The reaction mixture was treated in a similar manner to that of the Preparation 15-(2) to give the captioned compound (3.45 g.). mp>230° C.

I.R. (Nujol): 3150, 3080, 1720 cm$^{-1}$.

N.M.R. (DMSO-d$_6$):

δ(ppm) 3.60 (2H, s), 6.20–7.72 (6H, m).

Preparation 18

(1) Preparation of 2-oxo-3-methylthio-7-(3,4,5-trimethoxyphenoxy)indoline

Chlorine gas (1.4 g.), ethyl methylthioacetate (2.7 g.), 2-(3,4,5-trimethoxyphenoxy)aniline (11 g.), triethylamine (3.3 g.) and methylene chloride (40 ml.) were treated in a similar manner to that of the Preparation 15-(1) to give the captioned compound (2.7 g.). mp 155° to 158° C.

I.R. (Nujol): 3200, 3100, 1720 cm$^{-1}$.

N.M.R. (DMSO-d$_6$): δ(ppm) 2.00 (3H, s), 3.65 (3H, s), 3.73 (6H, s), 4.60 (1H, s), 6.35 (2H, s), 6.76–7.27 (3H, m).

(2) Preparation of 2-oxo-7-(3,4,5-trimethoxyphenoxy)indoline

A mixture of the above product (5 g.), Raney nickel (W-2 type)(8 ml.) and dioxane (80 ml.) was treated in a similar manner to that of the Preparation 15-(2) to give the captioned compound (3.2 g.). mp 170° to 171° C.

I.R. (Nujol): 3200, 3070, 1720 cm$^{-1}$.

N.M.R. (DMSO-d$_6$): δ(ppm) 3.58 (2H, s), 3.67 (3H, s), 3.74 (6H, s), 6.36 (2H, s), 6.76–7.12 (3H, m), 10.62 (1H, s).

Preparation 19

(1) Preparation of 2-oxo-3-methylthio-7-(2-pyridyloxy)indoline

Chlorine gas (1.7 g.), ethyl methylthioacetate (3.2 g), 2-(2-pyridyloxy)aniline (8.8 g.), triethylamine (3.8 g) and methylene chloride (70 ml.) were treated in a similar manner to that of the Preparation 15-(1) to give the captioned compound (2.95 g.). mp 140° to 142° C.

I.R. (Nujol): 3150, 3050, 1710 cm$^{-1}$.

N.M.R. (DMSO-d$_6$): (ppm) 2.01 (3H, s), 4.60 (1H, s), 6.94–7.25 (5H, m), 7.67–8.17 (2H, m).

(2) Preparation of 2-oxo-7-(2-pyridyloxy)indoline

A mixture of the above compound (4.1 g.), Raney nickel (W-2 type)(16 ml.) and dioxane (80 ml.) was treated in a similar manner to that of the Preparation 15-(2) to give the captioned compound (2.9 g.). mp 187° to 191° C.

I.R. (Nujol): 3150, 1700 cm$^{-1}$.

N.M.R. (DMSO-d$_6$): δ(ppm) 3.58 (2H, s), 6.94–7.20 (5H, m), 7.70–8.20 (2H, m), 10.58 (1H, broad s).

Preparation 20

(1) Preparation of 2-oxo-3-methylthio-7-benzyloxyindoline

Chlorine gas (740 mg.), ethyl methylthioacetate (1.4 g.), 2-benzyloxyaniline (4 g.), triethylamine (1.65 g.) and methylene chloride (35 ml.) were treated in a similar manner to that of the Preparation 15-(1) to give the captioned compound (2.1 g.). mp 127° to 129° C.

I.R. (Nujol): 3200, 3050, 1710 cm$^{-1}$.

N.M.R. (DMSO-d$_6$): δ(ppm) 2.00 (3H, s), 4.53 (1H, s), 5.23 (2H, s), 6.91–7.70 (8H, m).

(2) Preparation of 2-oxo-7-benzyloxyindoline

A mixture of the above product (3 g.), Raney nickel (W-2 type)(about 10 ml.) and dried ethanol (50 ml.) was treated in a similar manner to that of the Preparation 15-(2) to give the captioned compound (1.5 g.). mp 140° to 142° C.

I.R. (Nujol): 3200, 3050, 1700 cm$^{-1}$.

N.M.R. (DMSO-d$_6$): δ(ppm) 3.50 (2H, s), 5.18 (2H, s), 6.85–7.70 (8H, m).

Preparation 21

(1) Preparation of 2-oxo-3-methylthio-7-(2-aminophenoxy)indoline and bis(2-oxo-3-methylthioindolin-7-yl)ether Chlorine gas (8.85 g.), ethyl methylthioacetate (16.7 g.), bis(2-aminophenyl) ether (25 g), triethylamine (20 g.) and methylene chloride (190 ml.) were treated in a similar manner to that of the Preparation 15-(1). The resultant oily residue was dissolved in ethanol. To the solution was added a small amount of conc. hydrochloric acid and the mixture was allowed to stand under cooling. The precipitates were collected by filtration. To this product was added diluted hydrochloric acid, and then insoluble substances were collected by filtration, washed with ethanol and diethyl ether and dried to give bis(2-oxo-3-methylthioindolin-7-yl)ether (2.5 g.).

I.R. (Nujol): 3175, 1720, 1680 cm$^{-1}$.

N.M.R. (DMSO-d$_6$): (ppm) 2.05 (6H, s), 4.63 (2H, s), 6.50–7.30 (6H, m), 10.80 (2H, broad s).

On the other hand, ethyl acetate was added to the ethanol mother liquor obtained above and the mixture was allowed to stand at ambient temperature. The precipitates were collected by filtration, suspended in a saturated aqueous solution of sodium bicarbonate under warming and extracted with ethyl acetate. The extract was washed with water, dried over magnesium sulfate, treated with activated charcoal and then evaporated under reduced pressure. The residue was pulverized with diethyl ether to give 2-oxo-3-methylthio-7-(2-aminophenoxy)indoline (9.1 g.). mp 168° to 170° C.

I.R. (Nujol): 3450, 3350, 3150, 1690 cm$^{-1}$.

N.M.R. (DMSO-d$_6$): δ(ppm) 2.00 (3H, s), 3.78 (2H, broad s), 4.23 (1H, s), 6.59–7.25 (7H, m), 8.65 (1H, broad s).

(2) Preparation of 2-oxo-7-(2-aminophenoxy)indoline

A mixture of 2-oxo-3-methylthio-7-(2-aminophenoxy)indoline (4.5 g.), Raney nickel (W-2 type)(9 ml.) and dioxane (50 ml.) was treated in a similar manner to that of the Preparation 15-(2) to give the captioned compound (3.5 g.) mp 210° to 212° C.

I.R. (Nujol):

3450, 3350, 3150, 1690 cm$^{-1}$.

N.M.R. (DMSO-d$_6$): δ(ppm) 3.52 (2H, s), 5.91 (2H, broad s), 6.58–7.15 (7H, m), 10.56 (1H, s).

(3) Preparation of bis(2-oxoindolin-7-yl)ether

A mixture of bis(2-oxo-3-methylthioindolin-7-yl)ether (2.9 g.), Raney nickel (W-2 type)(14 ml.) and dioxane (100 ml.) was treated in a similar manner to that of the Preparation 15-(2) to give the captioned compound (2.4 g.) mp>230° C.

I.R. (Nujol): 3170, 1690, 1215 cm$^{-1}$.

N.M.R. (DMSO-d$_6$): δ(ppm) 3.55 (4H, s), 6.54–7.08 (6H, m).

Preparation 22

(1) Preparation of 2-oxo-3-methylthio-5-phenoxyindoline

Chlorine gas (2.35 g.), ethyl methylthioacetate (4.42 g.), 4-phenoxyaniline (12.2 g.), triethylamine (5.2 g.) and methylene chloride (105 ml.) were treated in a similar manner to that of the Preparation 15-(1) to give the captioned compound (6.65 g.). mp 124° to 128° C.

I.R. (Nujol): 3200, 3060, 1730 cm$^{-1}$.

N.M.R. (DMSO-d$_6$): (ppm) 1.90 (3H, s), 4.47 (1H, s), 6.80-7.57 (8H, m), 9.00 (1H, s).

(2) Preparation of 2-oxo-5-phenoxyindoline

A mixture of the above product (6.1 g.), Raney nickel (W-2 type)(13 ml.) and dioxane (100 ml.) was treated in a similar manner to that of the Preparation 15-(2) to give the captioned compound (3.7 g.). mp 148° to 150° C.

I.R. (Nujol): 3170, 3130, 3050, 1705 cm$^{-1}$.

N.M.R. (DMSO-d$_6$): δ(ppm) 3.47 (2H, s), 6.70-7.50 (8H, m), 10.36 (1H, s).

Preparation 23

(1) Preparation of 2-oxo-3-methylthio-5-(4-chlorophenoxy)indoline

Chlorine gas (2.6 g.), ethyl methylthioacetate (4.92 g.), 4-(4-chlorophenoxy)aniline (16 g.), triethylamine (5.9 g.) and methylene chloride (170 ml.) were treated in a similar manner to that of the Preparation 15-(1) to give the powdery crystals of the captioned compound (5.85 g.). mp 166° to 169° C.

I.R. (Nujol): 3180, 1710 cm$^{-1}$.

N.M.R. (DMSO-d$_6$): δ(ppm) 1.98 (3H, s), 4.55 (1H, s), 6.77-7.62 (7H, m), 10.58 (1H, broad s).

(2) Preparation 2-oxo-5-(4-chlorophenoxy)indoline

A mixture of the above product (5.8 g.), Raney nickel (W-2 type)(14 ml.) and dioxane (100 ml.) was treated in a similar manner to that of the Preparation 15-(2) to give the powdery crystals of the captioned compound (4.3 g.). mp 130° to 132° C.

I.R. (Nujol): 3170, 1710, 1480, 1230 cm$^{-1}$.

N.M.R. (DMSO-d$_6$): δ(ppm) 3.48 (2H, s), 6.70-7.58 (7H, m), 10.35 (1H, broad s).

Preparation 24

(1) Preparation of 2-oxo-3-methylthio-5-(2-chlorophenoxy)indoline

Chlorine gas (2.6 g.), ethyl methylthioacetate (4.92 g.), 4-(2-chlorophenoxy)aniline (16 g.), triethylamine (5.9 g.) and methylene chloride (120 ml.) were treated in a similar manner to that of the Preparation 15-(1) to give powdery crystals of the captioned compound (5.1 g.). mp 120° to 123° C.

I.R. (Nujol): 3200, 1730 cm$^{-1}$.

N.M.R. (CDCl$_3$): δ(ppm) 2.00 (3H, s), 4.26 (1H, s), 6.83-7.63 (7H, m), 9.68 (1H, broad s).

(2) Preparation of 2-oxo-5-(2-chlorophenoxy)indoline

A mixture of the above product (5 g.), Raney nickel (W-2 type)(12 ml) and dioxane (100 ml.) was treated in a similar manner to that of the Preparation 15-(2) to give the captioned compound (3.07 g.). mp 139° to 140° C.

I.R. (Nujol): 3150, 1710, 1480, 1200 cm$^{-1}$.

N.M.R. (DMSO-d$_6$): δ(ppm) 3.50 (2H, s), 6.78-7.70(7H, m), 9.43 (1H, broad s).

Preparation 25

(1) Preparation of 2-oxo-3-methylthio-7-anilinoindoline

Chlorine gas (4.2 g.), ethyl methylthioacetate (7.9 g.), 2-anilinoaniline (20 g.), triethylamine (9 g.) and methylene chloride (90 ml.) were treated in a similar manner to that of the Preparation 15-(1) to give the captioned compound (2.5 g.). mp 174° to 176° C.

I.R. (Nujol): 3360, 3180, 3050, 1690 cm$^{-1}$.

N.M.R. (DMSO-d$_6$): δ(ppm) 2.00 (3H, s), 4.48 (1H, s), 6.7-7.30 (8H, m), 7.31 (1H, s), 10.15 (1H, s).

(2) Preparation of 2-oxo-7-anilinoindoline

A mixture of the above product (4.1 g.), Raney nickel (W-2 type)(8 ml.) and dioxane (50 ml.) was treated in a similar manner to that of the Preparation 15-(2) to give the captioned compound (3 g.). mp 166° to 168° C.

I.R. (Nujol): 3400, 3160, 3050, 1700 cm$^{-1}$.

N.M.R. (DMSO-d$_6$): δ(ppm) 3.49 (2H, ABq), 6.64-7.40 (8H, m), 9.98 (1H, s).

Preparation 26

(1) Preparation of 2-oxo-3-methylthio-7-(2-chloroanilino)indoline

Chlorine gas (3.4 g.), ethyl methylthioacetate (6.4 g.), 2-(2-chloroanilino)aniline (21 g.), triethylamine (7.75 g.) and methylene chloride (100 ml.) were treated in a similar manner to that of the Preparation 15-(1) to give the captioned compound (7.3 g.). mp 151° to 153° C.

I.R. (Nujol): 3380, 3350, 3160, 1700 cm$^{-1}$.

N.M.R. (DMSO-d$_6$): δ(ppm) 2.08 (3H, s), 4.60 (1H, s), 6.70-7.58 (7H, m), 10.50 (1H, s).

(2) Preparation of 2-oxo-5-7-(2-chloroanilino)indoline

A mixture of the above product (7 g.), Raney nickel (W-2 type) (11 ml.) and dioxane (100 ml.) was treated in a similar manner to that of the Preparation 15-(2) to give the captioned compound (5.1 g.). mp 225° to 228° C.

I.R. (Nujol): 3380, 3170, 3130, 3050, 1690 cm$^{-1}$.

N.M.R. (DMSO-d$_6$): δ(ppm) 3.43 (2H, ABq), 6.66-7.52 (7H, m), 10.34 (1H, s).

Preparation 27

(1) Preparation of 2-oxo-3-methylthio-7-(4-chloroanilino)indoline

Chlorine gas (1.4 g.), ethyl methylthioacetate (2.64 g.), 2-(4-chloroanilino)aniline (85 g.), triethylamine (3.2 g.) and methylene chloride (180 ml.) were treated in a similar manner to that of the Preparation 15-(1) to give the captioned compound (2.0 g.) mp 190° to 192° C.

I.R. (Nujol): 3370, 3180, 3050, 1690 cm$^{-1}$.

N.M.R. (DMSO-d$_6$): δ(ppm) 2.00 (3H, s), 4.55 (1H, s), 6.79-7.32 (7H, m), 7.56 (1H, s), 10.25 (1H, s).

(2) Preparation of 2-oxo-7-(4-chloroanilino)indoline

A mixture of the above product (5 g.), Raney nickel (W-2 type)(15 ml.) and dioxane (100 ml.) was treated in a similar manner to that of the Preparation 15-(2) to give the captioned compound (3.2 g.). mp 190° to 192° C.

I.R. (Nujol): 3325, 3180, 1690 cm$^{-1}$.

N.M.R. (DMSO-d$_6$): δ(ppm) 3.48 (2H, s), 6.68-7.27 (7H, m), 7.44 (1H, s), 9.97 (1H, s).

Preparation 28

(1) Preparation of 2-oxo-7-phenylthioindoline

A suspension of iron powder (1.5 g.) and ammonium chloride (0.15 g.) in a mixture of ethanol (7 ml.) and water (7ml.) was refluxed with stirring. Ethyl 2-(2-nitro-3-phenylthiophenyl)acetate (1.6 g.) was added to the suspension, and the mixture was refluxed for 7 hours and filtered. The filtrate was evaporated to dryness under reduced pressure, and residue was dissolved in ethyl acetate. The solution was washed with water, dried over magnesium sulfate and evaporated under reduced pressure. The oily residue was dissolved in ethanol (10 ml.) and heated with conc. hydrochloric acid (0.1 ml.). The precipitating crystals were collected by filtration and dried to give the captioned compound (0.9 g.). mp 160° to 161° C.

I.R. (Nujol): 3150, 3130, 3060, 3040, 1700 cm$^{-1}$.

N.M.R. (DMSO-d$_6$): δ(ppm) 3.60 (2H, s), 6.87-7.47 (8H, m), 10.57 (1H, broad s).

(2) Preparation of 2-oxo-7-phenylsulfinylindoline m-Chloroperbenzoic acid (purity: 85%, 0.76 g.) was added to a solution of 2-oxo-7-phenylthioindoline (0.9 g.) in chloroform (20 ml.) with stirring under ice cooling. The mixture was stirred at the same temperature for an hour. To the reaction mixture was added chloroform (50 ml.), and the solution was washed with a saturated aqueous solution of sodium bicarbonate and water, dried over magnesium sulfate and then evaporated. The resultant crystals (1.0 g.) were recrystallized from dioxane twice to give white prisms of the captioned compound (0.6 g.).

I.R. (Nujol): 3150, 3120, 3050 (sh), 3040 cm$^{-1}$.

N.M.R. (CDCl$_3$) $\delta$(ppm) 3.40 (2H, s), 6.87–7.87 (8H, m), 9.23 (1H, broad s).

Preparation 29

(1) Preparation of 2-oxo-7-(2-chlorophenylthio)indoline

A mixture of iron powder (21.9 g.) and ammonium chloride (2.5 g.) in a mixture of ethanol (150 ml.) and water (50 ml.) and ethyl 2-[2-nitro-3-(2-chlorophenylthio)phenyl acetate (21.9 g.) was treated in a similar manner to that of the Preparation 28-(1) to give crystals of the captioned compound (15.7 g.). mp 178° to 180.5° C.

I.R. (Nujol): 3100, 3040, 1745, 1720 cm$^{-1}$.

N.M.R. (DMSO-d$_6$): $\delta$(ppm) 3.63 (2H, s), 6.50–7.70 (7H, m), 10.66 (1H, s).

(2) Preparation of 2-oxo-7-(2-chlorophenylsulfinyl)indoline

A solution of 2-oxo-7-(2-chlorophenylthio)indoline (1.0 g.) in chloroform (20 ml.) and m-chloroperbenzoic acid (purity: 85%, 0.73 g.) was treated in a similar manner to that of the Preparation 28-(2) to give crystals of the captioned compound (0.7 g.). mp 243° to 245° C.

I.R. (Nujol): 3160, 3120, 3070, 1700, 1025 cm$^{-1}$.

N.M.R. (CDCl$_3$): $\delta$(ppm) 3.47 (2H, s), 6.90–8.30 (7H, m), 9.10 (1H, broad s).

Preparation 30

(1) Preparation of ethyl 2-(2-nitro-3-phenylsulfonylphenyl)acetate

To a solution of ethyl 2-(2-nitro-3-phenylthiophenyl)acetate (9.60 g.) in methylene chloride (200 ml.) was added m-chloroperbenzoic acid (12.0 g.) with stirring at ambient temperature, and the mixture was stirred for 3 hours and allowed to stand over night. The reaction mixture was poured into water, washed with an aqueous solution of sodium bicarbonate, dried over magnesium sulfate and evaporated. The resultant crystals were recrystallized from methanol to give white prisms of the captioned compound (10.0 g.), mp 105° to 106° C.

I.R. (Nujol): 1730, 1550, 1380, 1190 cm$^{-1}$.

N.M.R. (DMSO-d$_6$): $\delta$(ppm) 1.13 (3H, t, J=7 Hz), 3.80 (2H, s), 4.10 (2H, q, J=7 Hz), 7.50–8.50 (5H, m).

(2) Preparation of 2-oxo-7-phenylsulfonylindoline

A solution of iron powder (15.0 g.) and ammonium chloride (2.0 g.) in a mixture of ethanol (200 ml.) and water (20 ml.) and ethyl 2-nitro-3-phenylsulfonylphenyl acetate (12.0 g.) was treated in a similar manner to that of the Preparation 28-(1) to give pale yellow crystals of the captioned compound (5.50 g.). mp 217° to 220° C.

I.R. (Nujol): 3360, 1740, 1720 cm$^{-1}$.

N.M.R. (DMSO-d$_6$): $\delta$(ppm) 3.56 (2H, s), 7.0–8.33 (8H, m), 10.23 (1H, s).

Preparation 31

Preparation of 2-oxo-5-chloro-7-(2-fluorophenyl)indoline

To a solution of ethyl 2-[2-amino-3-(2-fluorophenoxy)phenyl]acetate (8.5 g.) in dioxane (100 ml.) was added N-chlorosuccinimide (4.3 g.), and the mixture was stirred for an hour at 80° C. To the reaction mixture was added conc. hydrochloric acid (0.1 ml.), and the mixture was stirred for 10 minutes at ambient temperature. Dioxane was distilled off from the resulting mixture under reduced pressure. To the residue was added water and the mixture was extracted with ethyl acetate (200 ml.) twice. The extract was washed with a saturated aqueous solution of sodium chloride (100 ml.) twice, dried over magnesium sulfate and then evaporated under reduced pressure. The residue was washed with a mixture of diethyl ether and n-hexane (1:10) and recrystallized from ethanol to give crystals of 2-oxo-5-chloro-7-(2-fluorophenoxy)indoline (4.2 g.), mp 204° to 207° C.

I.R. (Nujol): 3180, 3050, 1700 cm$^{-1}$.

N.M.R. (DMSO-d$_6$): $\delta$(ppm) 3.60 (2H, s), 6.70–7.50 (6H, m).

Preparation 32

Preparation of 2-oxo-5-chloro-7-(2-chlorophenoxy)indoline

Ethyl 2-[2-amino-3-(2-chlorophenoxy)phenyl]acetate (1.50 g.), N-chlorosuccinimide (700 mg.) and dioxane (30 ml.) were treated in a similar manner to that of the Preparation 31 to give crystals of the captioned compound (0.50 g.), mp 196° to 198° C.

I.R. (Nujol): 3150, 1700, 1220, 1205 cm$^{-1}$.

N.M.R. (DMSO-d$_6$): $\delta$(ppm) 3.60 (2H, s), 6.67–7.73 (6H, m).

Preparation 33

Preparation of 1-[2-{2-nitro-3-(2-fluorophenoxy)phenyl}acetyl]-4-hydroxypiperidine A suspension of 2-[2-nitro-3-(2-fluorophenoxy)phenyl]acetic acid (5 g.) and phosphorus pentachloride (3.9 g.) in dry benzene (30 ml.) was stirred at ambient temperature for 30 minutes and then evaporated to give the acid chloride. A solution of the acid chloride in acetone (10 ml.) was added dropwise over 5 minutes to a solution of 4-hydroxypiperidine (2.6 g.) and sodium bicarbonate (5 g.) in a mixture of acetone (20 ml.) and water (50 ml.) at −2° to 0° C., stirred for an hour at ambient temperature and then evaporated. To the residue was added water and the mixture was extracted with ethyl acetate. The extract was washed with water, dried over magnesium sulfate and evaporated. The residue was dissolved in methanol and potassium hydroxide (1 g.) was added to the solution. The mixture was stirred for 2 hours at ambient temperature and evaporated. After addition of water to the residue, the mixture was extracted with ethyl acetate, and the extract was washed with water, dried over magnesium sulfate and then evaporated to give oily captioned compound (2.7 g.).

I.R. (Film): 3400, 1640, 1530, 1370, 1280 cm$^{-1}$.

N.M.R. (CDCl$_3$): $\delta$(ppm) 1.08–2.08 (4H, m), 2.78–4.19 (5H, m), 3.80 (2H, s), 6.64–7.50 (7H, m).

Preparation 34

Preparation of 1-[2-{2-nitro-3-(2-fluorophenoxy)phenyl}acetyl]-4-(2-hydroxyethyl)piperazine 2-[2-Nitro-3-(2-fluorophenoxy)phenyl]acetic acid (3.6 g.), phosphorus pentachloride (2.8 g.) and 2-(1-piperazinyl)ethanol (1.8 g.) were treated in a similar manner to that of the Preparation 33 to give the oily captioned compound (3.8 g.).

I.R. (Film): 3425, 1640, 1530, 1370, 1280 cm$^{-1}$.

N.M.R. (CDCl$_3$): δ(ppm) 2.43–2.65 (6H, m), 3.45–3.78 (8H, m), 6.73–7.50 (7H, m).

Prepartion 35

Preparation of N,N-diethyl-2-[2-nitro-3-(2-fluorophenoxy)phenyl]acetamide

2-[2-Nitro-3-(2-fluorophenoxy)phenyl]acetic acid (4 g.), phosphorus pentachloride (3.1 g.) and diethylamine (3 g.) were treated in a similar manner to that of the Preparation 33 to give the oily captioned compound (5.2 g.).

I.R. (Film): 1650, 1530, 1370, 1280 cm$^{-1}$.

N.M.R. (CCl$_4$) δ(ppm) 1.00–1.28 (6H, m), 3.37 (4H, q, J=7 Hz), 3.70 (2H, s), 6.70–7.47 (7H, m).

Preparation 36

(1) A mixture of powdered iron (20 g), ammonium chloride (2 g), ethanol (200 ml) and water (100 ml) was refluxed with stirring. To the mixture was added portionwise 2-nitrophenyl-2'-methoxyphenyl ether (20.1 g), and the mixture was refluxed with stirring for an hour. The hot reaction mixture was filtered and ethanol was distilled off from the filtrate. To the residue was added water and the mixture was extracted with diethyl ether. The extract was washed with saline, dried over magnesium sulfate and evaporated in vacuo to give oily substance (17.6 g). The oil was crystallized and then the solid was recrystallized from methanol (20 ml) to give crystals of 2-(2-methoxyphenoxy)aniline (13.0 g). mp 68°–70° C.

I.R. (NaCl, Nujol): 3500, 3400, 1630, 1600, 1590, 1500, 1460, 1440, 1330, 1300, 1260, 1220, cm$^{-1}$.

(2) A mixture of chlorine gas (2.1 g), ethyl methylthioacetate (4.0 g), 2-(2-methoxyphenoxy)aniline (13 g) and triethylamine (4.6 g) in methylene chloride (125 ml) were treated in a similar manner to that of the Preparation 15-(1) to give crystals of 2-oxo-3-methylthio-7-(2-methoxyphenoxy)indoline (3.9 g). mp 113.5°–114.5° C.

I.R. (NaCl, Nujol): 3100 (broad), 3050, 1715, 1635, 1600, 1500, 1460 (broad), 1280, 1260, 1205 cm$^{-1}$.

N.M.R. (DMSO-d$_6$): δ(ppm) 2.00 (3H, s), 3.77 (3H, s), 4.60 (1H, s), 6.40–7.33.(7H, m), 10.80 (1H, s).

Preparation 37

A mixture of chlorine gas (3 g), ethyl 2-methylthioacetate (5.65 g), 2-(α-naphthoxy)aniline (20 g) and triethylamine (6.7 g) in methylene chloride (140 ml) were treated in a similar manner to that of the Preparation 15-(1) to give 2-oxo-3-methylthio-7-(α-naphthoxy)indoline (5.7 g). mp 134°–139° C.

I.R. (NaCl, Nujol): 3200, 1720, 1460, 1390, 1200, 800, 770 cm$^{-1}$.

N.M.R. (DMSO-d$_6$): δ(ppm) 2.05 (3H, s), 4.66 (1H, s), 6.72–8.32 (10H, m).

Analysis for C$_{19}$H$_{15}$NO$_2$S: Calculated: C 71.02, H 4.71, N 4.36; Found: C 71.15, H 4.47, N 4.20.

Preparation 38

A mixture of chlorine gas (3 g), ethyl 2-methylthioacetate (5.65 g), 2-(β-naphthoxy)aniline (20 g) and triethylamine (6.7 ) in methylene chloride (170 ml) were treated in a similar manner to that of the Preparation 15-(1) to give 2-oxo-3-methylthio-7-(β-naphthoxy)indoline (7.6 g). mp 174°–175° C.

I.R. (NaCl, Nujol): 3300, 3050, 1700, 1640, 1500, 1470, 1220 cm$^{-1}$.

N.M.R. (DMSO-d$_6$): δ(ppm) 2.10 (3H, s), 4.68 (1H, s), 6.87–8.10 (10H, m).

Analysis for C$_{19}$H$_{15}$NO$_2$S Calculated: C 71.02, H 4.71, N 4.36; Found: C 70.77, H 4.38, N 4.16.

EXAMPLE 1

(1) Preparation of ethyl 2-(2-amino-3-phenoxyphenyl)acetate

To a mixture of iron powder (9 g.), ammonium chloride (0.9 g.), ethanol (80 ml.) and water (40 ml.) was added ethyl 2-(2-nitro-3-phenoxyphenyl)acetate (10.9 g.) over 5 minutes under mild reflux and stirring and the mixture was stirred for 1.5 hours at the same temperature. The reaction mixture was filtered under heating and ethanol was distilled off from the filtrate under reduced pressure. To the residue was added water and the mixture was extracted with diethyl ether. The extract was washed with water and dried over magnesium sulfate, and diethyl ether was distilled off under reduced pressure to give the viscous captioned compound (9.5 g.).

I.R. (Film): 3500, 3400, 1730 cm$^{-1}$.

(2) Preparation of sodium 2-(2-amino-3-phenoxyphenyl)acetate.

A mixture of ethyl 2-(2-amino-3-phenoxyphenyl)acetate (9.5 g.), sodium hydroxide (2.8 g.) and water (50 ml.) was refluxed under heating for 8 hours with stirring. The reaction mixture was left to cool at ambient temperature and adjusted to pH 7.5 with dilute hydrochloric acid. The resulting mixture was washed with ethyl acetate and then concentrated to dryness under reduced pressure. The residue was dissolved in methanol and insoluble materials were filtered off and then the filtrate was evaporated to dryness under reduced pressure. The residue was pulverized with ethyl acetate and the precipitates were collected by filtration, washed with ethyl acetate and dried to give white powder (9.4 g.). The powder was dissolved in water (120 ml.) and filtered, and the filtrate was lyophilized to give powder of the captioned compound (8.5 g.). mp 205° to 210° C.

I.R. (Nujol): 3350, 1580 cm$^{-1}$.

N.M.R. (DMSO-d$_6$): δ(ppm) 3.27 (2H, s), 5.33 (2H, s), 6.40–7.45 (8H, m).

EXAMPLE 2

(1) Preparation of ethyl 2-[2-amino-3-(2-fluorophenoxy)phenyl]acetate.

A mixture of iron powder (6 g.), ammonium chloride (0.6 g.), ethanol (40 ml.) and water (20 ml.) and ethyl 2-[2-nitro-3-(2-fluorophenoxy)phenyl]acetate (6.5 g.) were treated in a similar manner to that of Example 1-(1) to give oily captioned compound (5.7 g.).

I.R. (Film): 3450, 3400, 1730, 1260 cm$^{-1}$.

N.M.R. (DMSO-d$_6$): δ(ppm) 1.18 (3H, t, J=7 Hz), 3.67 (2H, s), 4.13 (2H, q, J=7 Hz), 4.85 (2H, s), 6.50–7.60 (7H, m).

(2) Preparation of 2-[2-amino-3-(2-fluorophenoxy)phenyl]acetic acid and its sodium salt A mixture of ethyl 2-[2-amino-3-(2-fluorophenoxy)phenyl]acetate (5.7 g.), sodium hydroxide (1.6 g.), water (25 ml.) and dioxane (25 ml.) was refluxed under heating for 16 hours with stirring. The reaction mixture was left to cool at ambient temperature and dioxane was distilled off under reduced pressure. To the residue was added water and the mixture was washed with diethyl ether. Diethyl ether was added to the aqueous layer and the mixture was adjusted to pH 3 to 4 with 5% sulfuric acid. The diethyl ether layer was separated, washed with water and dried over magnesium sulfate and then the solvent was distilled off under reduced pressure to give 2-[2-amino-3-(2-fluorophenoxy)phenyl]acetic acid (7 g.). This crude substance was recrystallized from a mixture of ethyl acetate and n-hexane to give the pure compound (3.6 g.), mp 122° to 123° C.

I.R. (Nujol): 3400, 3340, 2530, 1710 cm$^{-1}$.

Thus obtained compound was dissolved in a solution of sodium bicarbonate (1.16 g.) in water (50 ml.) and filtered. The filtrate was lyophilized to give sodium 2-[2-amino-3-(2-fluorophenoxy)phenyl]acetate (3.9 g.). mp 123° to 133° C.

I.R. (Nujol): 3450, 3350, 1570 cm$^{-1}$.

N.M.R. (DMSO-d$_6$): δ(ppm) 3.34 (2H, s), 5.30 (2H, broad s), 6.40–7.45 (7H, m).

EXAMPLE 3

(1) Preparation of ethyl 2-[2-amino-3-(4-chlorophenoxy)phenyl]acetate.

A mixture of iron powder (5.8 g.), ammonium chloride (0.6 g.), ethanol (60 ml.) and water (30 ml.) and ethyl 2-[2-nitro-3-(4-chlorophenoxy)phenyl]acetate (7.0 g.) were treated in a similar manner to that of Example 1-(1) to give oily captioned compound (5.9 g.).

I.R. (Film) 3450, 3400, 1730, 1230 cm$^{-1}$.

N.M.R. (DMSO-d$_6$): δ(ppm) 1.27 (3H, t, J=7 Hz), 3.57 (2H, s), 4.17 (2H, q, J=7 Hz), 4.30 (2H, broad s), 6.37–7.37 (7H, m).

(2) Preparation of sodium 2-[2-amino-3-(4-chlorophenoxy)phenyl]acetate.

A mixture of ethyl 2-[2-amino-3-(4-chlorophenoxy)phenyl]acetate (5.9 g.), sodium hydroxide (1.2 g.) and water (50 ml.) was treated in a similar manner to that of Example 1-(2). The resultant residue was pulverized with ethyl acetate to give white powder (2.2 g.). This substance was recrystallized from ethanol to give powdery crystals of the captioned compound (1.3 g.). mp 222° to 225° C.

I.R. (Nujol): 3420, 3350, 1570 cm$^{-1}$.

N.M.R. (DMSO-d$_6$): δ(ppm) 3.30 (2H, s), 5.35 (2H, broad s), 6.33–7.45 (7H, m).

EXAMPLE 4

(1) Preparation of ethyl 2-[2-amino-3-(3-chlorophenoxy)phenyl]acetate.

A mixture of iron powder (3.8 g.), ammonium chloride (0.4 g.), ethanol (40 ml.) and water (20 ml.) and ethyl 2-[2-nitro-3-(3-chlorophenoxy)phenyl]acetate (4.6 g.) were treated in a similar manner to that of Example 1-(1) to give oily captioned compound (4.0 g.).

I.R. (Film) 3450, 3400, 1730, 1230 cm$^{-1}$.

(2) Preparation of sodium 2-[2-amino-3-(3-chlorophenoxy)phenyl]acetate.

A mixture of ethyl 2-[2-amino-3-(3-chlorophenoxy)phenyl]acetate (4 g.), sodium hydroxide (1.05 g.) and water (30 ml.) was refluxed under heating for 17 hours with stirring. The reaction mixture was left to cool at ambient temperature, washed with ethyl acetate. To the aqueous solution was added ethyl acetate, and the mixture was adjusted to pH 4 to 5 with 5sulfuric acid. The ethyl acetate layer was separated, washed with water and dried over magnesium sulfate and then the solvent was distilled off under reduced pressure to given an oily residue. The residue was dissolved in a saturated aqueous solution of sodium bicarbonate, and the solution was washed with ethyl acetate and concentrated to dryness under reduced pressure. The residue was dissolved in methanol and filtered. The filtrate was concentrated under reduced pressure and the residue was crystallized with ethyl acetate to give white crystals of the captioned compound (1.3 g.). mp 119° to 124° C.

I.R. (Nujol): 3450, 3350, 1580 cm$^{-1}$.

N.M.R. (DMSO-d$_6$): δ(ppm) 3.39 (2H, s), 5.27 (2H, broad s), 6.44–7.40 (7H, m).

EXAMPLE 5

(1) Preparation of ethyl 2-[2-amino-3-(2-chlorophenoxy)phenyl]acetate

A mixture of iron powder (4.2 g.), ammonium chloride (0.42 g.), ethaol (60 ml.) and water (30 ml.) and ethyl 2-[2-nitro-3-(2-chlorophenoxy)phenyl]acetate (5 g.) were treated in a similar manner to that of Example 1-(1) to give oily captioned compound (4.3 g.).

I.R. (Film): 3450, 3400, 1730 cm$^{-1}$.

(2) Preparation of 2-[2-amino-3-(2-chlorophenoxy)phenyl]acetic acid and its sodium salt.

A mixture of ethyl 2-[2-amino-3-(2-chlorophenoxy)phenyl]acetate (4.3 g.), sodium hydroxide (1.1 g.) and water (50 ml.) was refluxed under heating for 5 hours with stirring. The reaction mixture was left to cool at ambient temperature and washed with diethyl ether. To the aqueous solution was added diethyl ether, and the mixture was adjusted to ph 4 with 5% sulfuric acid. The diethyl ether layer was separated, washed with water and dried over magnesium sulfate and then the solvent was distilled off under reduced pressure. The residue (3.4 g.) was crystallized with a mixture of benzene and n-hexane to give 2[2-amino-3-(2-chlorophenoxy)phenyl]acetic acid (1.9 g.). mp 86° to 90° C.

I.R. (Nujol): 3400, 3330, 2500, 1710 cm$^{-1}$.

Thus obtained compound was dissolved in a solution of sodium bicarbonate (575 mg.) in water (50 ml.) and filtered. The filtrate was lyophilized to give sodium 2-[2-amino-3-(2-chlorophenoxy)phenyl]acetate (1.9 g.).

I.R. (Nujol): 3350, 3200, 1570 cm$^{-1}$.

N.M.R. (DMSO-d$_6$): δ(ppm) 3.38 (2H, s), 5.10 (2H, broad s), 6.53–7.70 (7H, m).

EXAMPLE 6

(1) Preparation of ethyl 2-[2-amino-3-(3,4-dichlorophenoxy)phenyl]acetate.

A mixture of iron powder (6.2 g.), ammonium chloride (0.62 g.), ethanol (80 ml.) and water (40 ml.) and ethyl 2-[2-nitro-3-(3,4-dichlorophenoxy)phenyl]acetate (8 g.) were treated in a similar manner to that of Example 1-(1) to give oily captioned compound (7.2 g.).

I.R. (Film): 3450, 3400, 1730 cm$^{-1}$.

(2) Preparation of 2-[2-amino-3-(3,4-dichlorophenoxy)phenyl]acetic acid and its sodium salt.

A mixture of ethyl 2-[2-amino-3-(3,4-dichlorphenoxy)phenyl]acetate (7.2 g.), sodium hydroxide (1.7 g.) and water (50 ml.) was treated in a similar manner to that of Example 5-(2). The resultant residue was pulverized with benzene, and the precipitates were collected by filtration and dried to give 2-[2-amino-3-(3,4-dichlorophenoxy)phenyl]acetic acid (4.2 g.). mp 125° to 127° C.

I.R. (Nujol): 3410, 3340, 2550, 1720, 1250 cm$^{-1}$.

Thus obtained compound was dissolved under heating in a solution of sodium bicarbonate (1.08 g.) in water and filtered. The filtrate was lyophilized to give sodium 2-[2-amino-3-(3,4-dichlorophenoxy)phenyl]acetate (4.1 g.), mp 200° to 205° C.

I.R. (Nujol): 3350, 1570 cm$^{-1}$.

N.M.R. (DMSO-d$_6$): (ppm) 3.25 (2H, s), 5.35 (2H, broad s), 6.35–7.61 (6H, m).

EXAMPLE 7

(1) Preparation of ethyl 2-[2-amino-3-(3,5-dichlorophenoxy)phenyl]acetate.

A mixture of iron powder (7 g.), ammonium chloride (0.7 g.), ethanol (80 ml.) and water (40 ml.) and ethyl 2-[2-nitro-3-(3,5-dichlorophenoxy)phenyl]acetate (7.6 g.) were treated in a similar manner to that of Example 1-(1) to give oily captioned compound (6.9 g.).

I.R. (Film): 3450, 3400, 1730 cm$^{-1}$.

(2) Preparation of 2-[2-amino-3-(3,5-dichlorophenoxy)phenyl]acetic acid and its sodium salt.

A mixture of ethyl 2-[2-amino-3-(3,5-dichlorophenoxy)phenyl]acetate (6.9 g.), sodium hydroxide (1.6 g.) and water (50 ml.) was treated in a similar manner to that of Example 5-(2). The resultant residue (6.2 g.) was crystallized with a mixture of ethyl acetate and n-hexane to give white crystals of 2-[2-amino-3-(3,5-dichlorophenoxy)phenyl]acetic acid (4.5 g.). mp 113° to 115° C.

I.R. (Nujol): 3450, 3360, 1720 cm$^{-1}$.

N.M.R. (DMSO-d$_6$): δ(ppm) 3.53 (2H, s), 6.41–7.27 (6H, m)

Thus obtained compound (3.1 g.) was dissolved in a solution of sodium bicarbonate (840 mg.) in water (60 ml.) and filtered. The filtrate was concentrated to dryness under reduced pressure and the residue was crystallized with ethyl acetate to give sodium 2-[2-amino-3-(3,5-dichlorophenoxy)phenyl]acetate. mp 184° to 191° C.

I.R. (Nujol): 3450, 3380, 3300, 1590, 1580, 1570 cm$^{-1}$.

N.M.R. (DMSO-d$_6$): δ(ppm) 3.33 (2H, s), 5.47 (2H, broad s), 6.43–7.30 (6H, m).

EXAMPLE 8

(1) Preparation of ethyl 2-[2-amino-3-(2,3-dichlorophenoxy)phenyl]acetate.

A mixture of iron powder (4 g.), ammonium chloride (0.4 g.), ethanol (50 ml.) and water (25 ml.) and ethyl 2-[2-nitro-3-(2,3-dichlorophenoxy)phenyl]acetate (4.3 g.) were treated in a similar manner to that of Example 1-(1) to give oily captioned compound (3.7 g.).

I.R. (Film): 3500, 3400, 1730 cm$^{-1}$.

(2) Preparation of 2-[2-amino-3-(2,3-dichlorophenoxy)phenyl]acetic acid and its sodium salt.

A mixture of ethyl 2-[2-amino-3-(2,3-dichlorophenoxy)phenyl]acetate (3.7 g.), sodium hydroxide (880 mg.) and water (50 ml.) was treated in a similar manner to that of Example 5-(2). The resultant residue was pulverized with benzene, and the precipitates were collected by filtration and dried to give 2-[2-amino-3-(2,3-dichlorophenoxy)phenyl]acetic acid (2.65 g.).

I.R. (Nujol): 3400, 3320, 2500, 1700 cm$^{-1}$.

Thus obtained compound was dissolved in a solution of sodium bicarbonate (715 mg.) in water (60 ml.) and filtered. The filtrate was lyophilized to give sodium 2-[2-amino-3-(2,3-dichlorophenoxy)phenyl]acetate (2.2 g.).

I.R. (Nujol): 3400, 1570 cm$^{-1}$.

N.M.R. (DMSO-d$_6$): δ(ppm) 3.32 (2H, s), 5.47 (2H, broad s), 6.42–7.47 (6H, m).

EXAMPLE 9

(1) Preparation of ethyl 2-[2-amino-3-(2,4-dichlorophenoxy)phenyl]acetate.

A mixture of iron powder (3.6 g.), ammonium chloride (0.36 g.), ethanol (50 ml.) and water (25 ml.) and ethyl 2-[2-nitro-3-(2,4-dichlorophenoxy)phenyl]acetate (3.9 g.) were treated in a similar manner to that of Example 1-(1) to give oily captioned compound (3.5 g.).

I.R. (Film): 3450, 3400, 1730 cm$^{-1}$.

(2) Preparation of 2-[2-amino-3-(2,4-dichlorophenoxy)phenyl]acetic acid and its sodium salt.

A mixture of ethyl 2-[2-amino-3-(2,4-dichlorophenoxy)phenyl]acetate (3.1 g.), sodium hydroxide (730 mg.) and water (40 ml.) was treated in a similar manner to that of Example 5-(2). The resultant residue was pulverized with benzene, collected by filtration and dried to give 2-[2-amino-3-(2,4-dichlorophenoxy)phenyl]acetic acid (2.1 g.). mp 123° to 124° C.

I.R. (Nujol): 3400, 3320, 2530, 1700 cm$^{-1}$.

Thus obtained compound was dissolved in a solution of sodium bicarbonate (565 mg.) in water (50 ml.) and filtered. The filtrate was lyophilized to give sodium 2-[2-amino-3-(2,4-dichlorophenoxy)phenyl]acetate (2.2 g.).

I.R. (Nujol): 3350, 3200, 1570 cm$^{-1}$.

N.M.R. (DMSO-d$_6$): δ(ppm) 3.40 (2H, s), 4.75 (2H, broad s), 6.37–7.74 (6H, m).

EXAMPLE 10

(1) Preparation of ethyl 2-[2-amino-3-(o-tolyloxy)phenyl]acetate.

A mixture of iron powder (2.1 g.), ammonium chloride (0.21 g.), ethanol (40 ml.) and water (20 ml.) and ethyl 2-[2-nitro-3-(o-tolyloxy)phenyl]acetate (3.4 g.) were treated in a similar manner to that of Example 1-(1) to give oily captioned compound (3.1 g.).

I.R. (Film): 3470, 3400, 1730 cm$^{-1}$.

N.M.R. (CCl$_4$-D$_2$O): δ(ppm) 1.27 (3H, t, J=7 Hz), 2.27 (3H, s), 3.53 (2H, s), 4.12 (2H, q, J=7 Hz), 6.43–7.27 (7H, m).

(2) Preparation of 2-[2-amino-3-(o-tolyloxy)phenyl]acetic acid and its sodium salt.

A mixture of ethyl 2-[2-amino-3-(o-tolyloxy)phenyl]acetate (3.1 g.), sodium hydroxide (0.9 g.), water (20 ml.) and dioxane (20 ml.) was treated in a similar manner to that of Example 2-(2) to give crystals of 2-[2-amino-3-(o-tolyloxy)phenyl]acetic acid (2.0 g.). Thus obtained compound was dissolved in a solution of sodium bicarbonate (0.343 g.) in water (50 ml.) under heating and filtered. The filtrate was lyophilized to give sodium 2-[2-amino-3-(o-tolyloxy)phenyl]acetate (1.1 g.). mp >150° C.

I.R. (Nujol): 3600, 3340, 3180, 1570 cm$^{-1}$.

N.M.R. (DMSO-d$_6$): δ(ppm) 2.27 (3H, s), 3.23 (2H, s), 5.50 (2H, broad s), 6.40–7.40 (7H, m).

EXAMPLE 11

(1) Preparation of ethyl 2-[2-amino-3-(3,4-dimethylphenoxy)phenyl]acetate.

A mixture of iron powder (3 g.), ammonium chloride (0.3 g.), ethanol (40 ml.) and water (20 ml.) and ethyl 2-[2-nitro-3-(3,4-dimethylphenoxy)phenyl]acetate (3.6 g.) were treated in a similar manner to that of Example 1-(1) to give oily captioned compound (3.2 g.).

I.R. (Film): 3450, 3400, 1730 cm$^{-1}$.

(2) Preparation of 2-[2-amino-3-(3,4-dimethylphenoxy)phenyl]acetic acid and its sodium salt A mixture of ethyl 2-[2-amino-3-(3,4-dimethylphenoxy)phenyl]acetate (3.2 g.), sodium hydroxide (0.9 g.) and water (50 ml.) was treated in a similar manner to that of Example 5-(2). The resultant residue was crystallized with a mixture of benzene and n-hexane to give 2-[2-amino-3-(3,4-dimethylphenoxy)phenyl]acetic acid (2.1 g.). mp 90° to 92° C.

I.R. (Nujol): 3550, 3400, 3340, 1710 cm$^{-1}$.

Thus obtained compound was dissolved in a solution of sodium bicarbonate (650 mg.) in water (50 ml.) and filtered. The filtrate was lyophilized to give sodium 2-[2-amino-3-(3,4-dimethylphenoxy)phenyl]acetate (2.2 g.).

I.R. (Nujol): 3350, 3200, 1570 cm$^{-1}$

N.M.R. (DMSO-d$_6$): δ(ppm) 2.15 (6H, s), 3.33 (2H, s), 5.10 (2H, broad s), 6.32–7.09 (6H, m).

EXAMPLE 12

(1) Preparation of ethyl 2-(2-amino-3-phenylthiophenyl)acetate.

A mixture of iron powder (5.7 g.), ammonium chloride (0.57 g.), ethanol (50 ml.) and water (25 ml.) and ethyl 2-(2-nitro-3-phenylthiophenyl)acetate (7.2 g.) were treated in a similar manner to that of Example 1-(1) to give oily captioned compound (6.2 g.).

I.R. (Film): 3430, 3400, 1730 cm$^{-1}$.

(2) Preparation of sodium 2-(2-amino-3-phenylthiophenyl)acetate.

A mixture of ethyl 2-(2-amino-3-phenylthiophenyl)acetate (6.2 g.), sodium hydroxide (1.7 g.) and water (50 ml.) was treated in a similar manner to that of Example 1-(2) to give the captioned compound (5.4 g.). mp 218° to 221° C.

I.R. (Nujol): 3400, 3330, 1580 cm$^{-1}$.

N.M.R. (DMSO-d$_6$): δ(ppm) 3.28 (2H, s), 5.95 (2H, broad s), 6.56–7.45 (8H, m).

EXAMPLE 13

(1) Preparation of ethyl 2-[2-amino-3-(4-chlorophenylthio)phenyl]acetate.

A mixture of iron powder (9 g.), ammonium chloride (0.9 g.), ethanol (80 ml.) and water (40 ml.) and ethyl 2-[2-nitro-3-(4-chlorophenylthio)phenyl]acetate (9.8 g.) were treated in a similar manner to that of Example 1-(1) to give oily captioned compound (8.3 g.)

I.R. (Film): 3480, 3400, 1720 cm$^{-1}$.

(2) Preparation of sodium 2-[2-amino-3-(4-chlorophenylthio)phenyl]acetate.

A mixture of ethyl 2-[2-amino-3-(4-chlorophenylthio)phenyl]acetate (8.3 g.), sodium hydroxide (2.1 g.) and water (50 ml.) was treated in a similar manner to that of Example 1-(2) to give the crude captioned compound (3.5 g.). This product was crystallized with a mixture of ethanol and ethyl acetate to give white needles of the captioned compound (2.4 g.). mp>230° C.

I.R. (Nujol): 3420, 3320, 1580 cm$^{-1}$.

N.M.R. (DMSO-d$_6$): δ(ppm) 3.27 (2H, s), 5.98 (2H, broad s), 6.46–7.60 (7H, m).

EXAMPLE 14

Preparation of 1-[2-{2-amino-3-(2-fluorophenoxy)phenyl}acetyl]-4-hydroxypyperidine hydrochloride A mixture of iron powder (2.7 g.), ammonium chloride (0.3 g.), ethanol (20 ml.) and water (10 ml.) and a solution of 1-[2-{2-nitro-3-(2-fluorophenoxy)phenyl}acetyl]-4-hydroxypiperidine (2.7 g.) in ethanol (5 ml.) were treated in a similar manner to that of Example 1-(1) to give oily 1-[2-{2-amino-3-(2-fluorophenoxy)phenyl}acetyl]-4-hydroxypiperidine (2.5 g.). Thus obtained compound was dissolved in ethanol containing hydrochloric acid and evaporated under reduced pressure. The residue was crystallized with a mixture of ethanol and ethyl acetate to give white needles of the captioned compound (2 g.). mp 160° to 161° C.

I.R. (Nujol): 3425, 2600, 1645, 1620, 1275 cm$^{-1}$.

N.M.R. (DMSO-d$_6$): (ppm) 6.25–7.65 (7H, m), 7.75 (4H, s).

EXAMPLE 15

Preparation of 1-[2-{2-amino-3-(2-fluorophenoxy)phenyl}acetyl]-4-(2-hydroxyethyl)piperazine A mixture of iron powder (3.7 g.), ammonium chloride (0.4 g.), ethanol (20 ml.) and water (10 ml.) and a solution of 1-[2-{2-nitro-3-(2-fluorophenoxy)phenyl}acetyl]-4-(2-hydroxyethyl)piperazine (3.7 g.) in ethanol (5 ml.) were treated in a similar manner to that of Example 1-(1) [extraction solvent: ethyl acetate] to give oily substance (1.9 g.). This substance was dissolved in methanol and water was added. The resultant mixture was concentrated under reduced pressure. After cooling, the precipitates were collected by filtration, washed with water and dried to give white needles of the captioned compound (1.6 g.). mp 86° to 92° C.

I.R. (KBr): 3500, 3400, 1625, 1270 cm$^{-1}$.

N.M.R. (DMSO-d$_6$): δ(ppm) 2.17–2.77 (6H, m), 3.35–3.85 (8H, m), 4.87 (2H, broad s), 6.40–7.57 (7H, m).

EXAMPLE 16

Preparation of N,N-diethyl-2-[2-amino-3-(2-fluorophenoxy)phenyl]acetamide hydrochloride.

A mixture of iron powder (5 g.), ammonium chloride (0.5 g.), ethanol (40 ml.) and water (20 ml.) and a solution of N,N-diethyl-2-[2-nitro-3-(2-fluorophenoxy)phenyl]acetamide (5.1 g.) in ethanol (5 ml.) were treated in a similar manner to that of Example 1-(1) [extraction solvent: ethyl acetate] to give oily N,N-diethyl-2-[2-amino-3-(2-fluorophenoxy)phenyl]acetamide (4.6 g.). This substance was dissolved in a mixture of methanol and hydrochloric acid. The solution was evaporated and the residue was pulverized with ethyl acetate. The resultant product (4.15 g.). was recrystallized from a mixture of ethanol and ethyl acetate to give white needles of the captioned compound (2.95 g.). mp 159° to 160° C.

I.R. (Nujol): 2700, 2550, 1630, 1610, 1270 cm$^{-1}$.

N.M.R. (DMSO-d$_6$): δ(ppm) 1.03 (3H, t, J=7 Hz), 1.13 (3H, t, J=7 Hz), 3.32 (2H, q, J=7 Hz), 3.43 (2H, q, J=7 Hz), 4.08 (2H, s), 6.58–7.63 (6H, m), 7.29 (3H, s).

EXAMPLE 17

Preparation of sodium 2-(2-amino-3-phenoxyphenyl)acetate

To a mixture of ethanol (50 ml.) and water (50 ml.) were added 2-oxo-7-phenoxyindoline (20.7 g.) and sodium hydroxide (14.8 g.). The mixture was refluxed under heating for 30 hours with stirring. After cooling, the reaction mixture was filtered and ethanol was distilled off from the filtrate. The remaining aqueous solution was adjusted to pH 8.3 with conc. hydrochloric acid and filtered. The filtrate was washed with diethyl ether and concentrated to dryness under reduced pressure. The residue was dissolved in ethanol and filtered, and the filtrate was evaporated under reduced pressure. The oily residue was crystallized with ethyl acetate. The resultant substance (17.8 g.) was dissolved in water and filtered. The filtrate was lyophilized to give powdery captioned compound (17.6 g.). mp 205° to 208° C.

I.R. (Nujol): 3350, 1580 cm$^{-1}$.

N.M.R. (DMSO-d$_6$): δ(ppm) 3.27 (2H, s), 5.33 (2H, broad s), 6.40–7.45 (8H, m).

EXAMPLE 18

Preparation of sodium 2-[2-amino-3-(2-chlorophenoxy)phenyl]propionate

A mixture of 2-oxo-3-methyl-7-(2-chlorophenoxy)indoline (4 g.), sodium hydroxide (2.4 g.), dioxane (25 ml.) water (25 ml.) was refluxed under heating for 5 days with stirring. After cooling, the reaction mixture was filtered and the filtrate was evaporated under reduced pressure. To the residue was added water and the mixture was washed with diethyl ether. Ethyl acetate was added to the aqueous solution and adjusted to pH 4 to 5 with 5% sulfuric acid. The ethyl acetate layer was separated, washed with water and dried over magnesium sulfate and the solvent was distilled off under reduced pressure to give oily 2-[2-amino-3-(2-chlorophenoxy)phenyl]propionic acid (2.4 g.). This compound was dissolved in an aqueous solution of sodium bicarbonate and filtered. The filtrate was concentrated to dryness under reduced pressure and the residue was dissolved in ethyl acetate and filtered. The filtrate was evaporated under reduced pressure, and the residue was dissolved in water and lyophilized to give light brown powder of the captioned compound (1.6 g.).

I.R. (Nujol): 3350, 3200, 1570 cm$^{-1}$.

N.M.R. (DMSO-d$_6$): δ(ppm) 1.53 (3H, d, J=7 Hz), 3.55 (1H, q, J=7 Hz), 5.50 (2H, broad s), 6.50–7.73 (7H, m).

EXAMPLE 19

Preparation of sodium 2-[2-amino-3-(2,6-dichlorophenoxy)phenyl]acetate.

A mixture of 2-oxo-7-(2,6-dichlorophenoxy)indoline (3.4 g.), sodium hydroxide (1.86 g.) and water (50 ml.) was refluxed under heating for 120 hours with stirring. Insoluble starting material (2.5 g.) was recovered by filtration and the filtrate was cooled. The precipitates were collected by filtration and washed with a small amount of water and diethyl ether in turn to give the captioned compound (1.35 g.). Further, to the above obtained insoluble material (2.5 g.) were added sodium hydroxide (2 g.) and 50% dioxane (50 ml.), and the mixture was stirred for 70 hours and filtered. After cooling, the precipitates were collected by filtration and washed with water and diethyl ether in turn to give the same captioned compound (1.3 g.). Total yield (2.65 g.). mp>230° C.

I.R. (Nujol): 3400, 3300, 1590 cm$^{-1}$.

N.M.R. (DMSO-d$_6$): δ(ppm) 3.28 (2H, s), 5.90–7.77 (6H, m).

EXAMPLE 20

Preparation of 2-[2-amino-3-(3,4,5-trimethoxyphenoxy)phenyl]acetic acid and its sodium salt A mixture of 2-oxo-7-(3,4,5-trimethoxyphenoxy)indoline (3.2 g.), sodium hydroxide (1 g.), dioxane (20 ml.) and water (20 ml.) was refluxed under heating for 36 hours with stirring. After cooling, the reaction mixture was washed with diethyl ether. Ethyl acetate was added to the aqueous solution and adjusted to pH 4.0 with 5% sulfuric acid. The ethyl acetate layer was separated, washed with water and dried over magnesium sulfate and the solvent was distilled off under reduced pressure. The residue was pulverized with diethyl ether to give 2-[2-amino-3-(3,4,5-trimethoxyphenoxy)phenyl]acetic acid (2.5 g.).

I.R. (Nujol): 3450, 3380, 1690 cm$^{-1}$.

Thus obtained substance was dissolved in a solution of sodium bicarbonate (630 mg.) in water (50 ml.) and filtered. The filtrate was lyophilized to give sodium 2-[2-amino-3-(3,4,5-trimethoxyphenoxy)phenyl]acetate (2.5 g.).

I.R. (Nujol): 3350, 3200, 1600 cm$^{-1}$.

N.M.R. (DMSO-d$_6$): δ(ppm) 3.30 (2H, s), 3.64 (3H, s), 3.70 (6H, s), 6.30 (2H, s), 6.40–6.85 (3H, m).

EXAMPLE 21

Preparation of sodium 2-[2-amino-3-(2-pyridyloxy)phenyl]acetate

A mixture of 2-oxo-7-(2-pyridyloxy)indoline (2.9 g.), sodium hydroxide (1.3 g.), dioxane (20 ml.) and water (20 ml.) was refluxed under heating for 16 hours with stirring. Dioxane was distilled off from the reaction mixture under reduced pressure, and water was added to the residue. The solution was washed with ethyl acetate and filtered, and the filtrate was cooled. The precipitates were collected by filtration, washed with a small amount of cold water and dried to give needles of the captioned compound (2.85 g.). mp 245° to 248° C.

I.R. (Nujol): 3350, 1600 cm$^{-1}$.

N.M.R. (DMSO-d$_6$): δ(ppm) 3.33 (2H, s), 6.40–7.23 (5H, m), 7.70–8.27 (2H, m).

EXAMPLE 22

Preparation of 2-(2-amino-3-benzyloxyphenyl)acetic acid and its sodium salt

A mixture of 2-oxo-7-benzyloxyindoline (2.15 g.), sodium hydroxide (0.84 g.), dioxane (20 ml.) and water (20 ml.) was refluxed under heating for 72 hours with stirring. After cooling, the reaction mixture was evaporated under reduced pressure. The residue was dissolved in water and the solution was washed with ethyl acetate. Diethyl ether was added to the solution and adjusted to pH 4 to 5 with 5% sulfuric acid. The diethyl ether layer was separated, washed with water, dried over magnesium sulfate and then evaporated under reduced pressure. The residue was crystallized with a mixture of ethyl acetate and n-hexane to give 2-(2-amino-3-benzyloxyphenyl)acetic acid (2.2 g.).

I.R. (Nujol): 3410, 3340, 2500, 1710 cm$^{-1}$.

Thus obtained product was dissolved in a solution of sodium bicarbonate (655 mg.) in water (50 ml.) and filtered. The filtrate was lyophilized to give sodium 2-(2-amino-3-benzyloxyphenyl)acetate (2.2 g.). mp 208° to 210° C.

I.R. (Nujol): 3400, 1590, 1560 cm$^{-1}$.

N.M.R. (DMSO, d$_6$): δ(ppm) 3.23 (2H, s), 4.20 (2H, broad s), 5.05 (2H, s), 6.31–6.84(3H, m), 7.27–7.75 (5H, m).

EXAMPLE 23

Preparation of sodium 2-[2-amino-3-(2-aminophenoxy)phenyl]acetate

A mixture of 2-oxo-7-(2-aminophenoxy)indoline (3.5 g.), sodium hydroxide (1.2 g.), dioxane (10 ml.) and water (50 ml.) was refluxed under heating for 48 hours with stirring. After cooling, the reaction mixture was filtered, and the filtrate was concentrated under reduced pressure. The residue was dissolved in ethanol under warming and filtered. The filtrate was concentrated under reduced pressure, and the residue was crystallized with a mixture of ethanol and ethyl acetate to give the captioned compound (3 g.). mp 103° to 110° C.

I.R. (Nujol): 3430, 3350, 1565 cm$^{-1}$.
N.M.R. (DMSO-d$_6$): (ppm) 3.33 (2H, s), 4.85 (2H, broad s), 5.10 (2H, broad s), 6.20-7.00 (7H, m).

EXAMPLE 24

Preparation of bis(2-amino-3-carboxymethylphenyl)ether and its disodium salt

A mixture of bis(2-oxoindolin-7-yl)ether (2.4 g.), sodium hydroxide (1.35 g.), dioxane (10 ml.) and water (50 ml.) was refluxed under heating for 7 hours with stirring. After cooling, the reaction mixture was filtered, the filtrate was concentrated under reduced pressure. The residue was dissolved in water and washed with ethyl acetate. Ethyl acetate was added to the solution and adjusted to pH 4 to 5 with 5% sulfuric acid. The ethyl acetate layer was separated, washed with water, dried over magnesium sulfate and then evaporated under reduced pressure. The residue was washed with a mixture of ethyl acetate and diethyl ether to give bis(2-amino-3-carboxymethylphenyl)ether (1.6 g.). mp22 240° C.

I.R. (Nujol): 3370, 3280, 2600, 2500, 1720, 1700 1470, 1265 cm$^{-1}$.

Thus obtained substance (1.6 g.) was dissolved in a solution of sodium hydroxide (404 mg.) in water (25 ml.) and water was distilled off under reduced pressure. The residue was crystallized with a mixture of methanol and ethanol to give disodium salt of bis(2-amino-3-carboxylmethylphenyl)ether (1.1 g.). mp>240° C.

I.R. (Nuzol): 3450, 3370, 1610, 1570 cm$^{-1}$.
N.M.R. (DMSO-d$_6$): δ(ppm) 3.22 (4H, s), 3.96 (4H, broad s), 6.31-6.85 (6H, m).

EXAMPLE 25

Preparation of sodium 2-(2-amino-5-phenoxyphenyl)acetate

A mixture of 2-oxo-5-phenoxyindoline (3.5 g.), sodium hydroxide (1.24 g), dioxane (20 ml.) and water (20 ml.) was refluxed under heating for a week with stirring. The reaction mixture was concentrated to dryness and the residue was dissolved in water (50 ml.) under heating and filtered. The filtrate was washed with diethyl ether and evaporated. The residue was dissolved in ethanol (100 ml.) under heating and filtered. The filtrate was concentrated at ordinal pressure to a volume of 30 ml. The concentrate was allowed to stand for one day at ambient temperature, and the precipitates were collected by filtration to give crystals of the captioned compound (2.5 g.). mp 239° to 242° C.

I.R. (Nujol): 3400, 3330, 1660, (sh), 1580, 1565 cm$^{-1}$.
N.M.R. (DMSO-d$_6$):
δ(ppm) 3.10 (2H, s), 6.40-7.40 (8H, m).

EXAMPLE 26

Preparation of sodium 2-[2-amino-5-(4-chlorophenoxy)phenyl]acetate

A mixture of 2-oxo-5-(4-chlorophenoxy)indoline (4.2 g.), sodium hydroxide (2.6 g.), dioxane (20 ml.) and water (40 ml.) was refluxed under heating for 5 days with stirring. After cooling, the reaction mixture was filtered and the filtrate was evaporated under reduced pressure. The residue was dissolved in water (50 ml.) and filtered. The filtrate was washed with diethyl ether and evaporated. The residue was dissolved in ethyl acetate (200 ml.) under warming and filtered. The filtrate was cooled, and the precipitating crystals were collected by filtration, washed with ethyl acetate and then recrystallized from a mixture of ethanol and ethyl acetate to give the captioned compound (3.4 g.). mp 206° to 209° C.

I.R. (Nujol): 3400, 3330, 1580, 1565, 1240 cm$^{-1}$.
N.M.R. (DMSO-d$_6$): δ(ppm) 3.20 (2H, s), 5.10 (2H, broad s), 6.50-7.60 (7H, m).

EXAMPLE 27

Preparation of sodium 2-[2-amino-5-(2-chlorophenoxy)phenyl]acetate

A mixture of 2-oxo-5-(2-chlorophenoxy)indoline (3.2 g.), sodium hydroxide (2 g.), dioxane (20 ml.) and water (40 ml.) was refluxed under heating for 5 days with stirring. After cooling, the reaction mixture was filtered. The filtrate was evaporated under reduced pressure. The residue was dissolved in ethyl acetate under warming and filtered. The filtrate was cooled in an ice bath and the precipitating crystals were collected by filtration, washed with ethyl acetate and then recrystallized from a mixture of methanol and ethyl acetate to give the captioned compound (3.2 g.). mp 105° to 115° C.

I.R. (Nujol): 3250, 1560, 1250 cm$^{-1}$.
N.M.R. (DMSO-d$_6$): δ(ppm) 3.22 (2H, s), 5.43 (2H, broad s), 6.50-7.70 (7H, m).

EXAMPLE 28

Preparation of 2-[2-amino-3-(2-chlorophenoxy)-5-chlorophenyl]acetic acid and its sodium salt A mixture of 2-oxo-5-chloro-7-(2-chlorophenoxy)indoline (2.0 g.), sodium hydroxide (0.50 g.), dioxane (20 ml.) and water (30 ml.) was refluxed under heating for 23 hours. The reaction mixture was evaporated under reduced pressure and the residue was dissolved in water and filtered. The filtrate was washed with diethyl ether, and diethyl ether was added to the aqueous layer and adjusted to pH 5 with 1N-sulfuric acid. The diethyl ether layer was separated, washed with water, dried over magnesium sulfate and then evaporated. The residue was recrystallized from ethanol to give crystals of 2-[2-amino-3-(2-chlorophenoxy)-5-chlorophenyl]acetic acid (0.725 g.).

I.R. (Nujol): 3500, 3380, 3300, 2550, 1700, 1240, 1220 cm$^{-1}$.

Thus obtained substance was dissolved in 1N-aqueous sodium hydroxide (2.4 ml.) and the solution was cooled and the precipitating crystals were collected by filtration to give sodium 2-[2-amino-3-(2-chlorophenoxy)-5-chlorophenyl]acetate (0.70 g.). mp 278° to 280° C.

I.R. (Nujol): 3600, 3200 (broad), 1220 cm$^{-1}$.
N.M.R. (DMSO-d$_6$): δ(ppm) 3.30 (2H, s), 5.50 (2H, broad s), 6.50-7.67 (6H, m).

EXAMPLE 29

Preparation of 2-[2-amino-3-(2-fluorophenoxy)-5-chlorophenyl]acetic acid and its sodium salt A mixture of 2-oxo-5-chloro-7-(2-fluorophenoxy)indoline (4.0 g.), sodium hydroxide (1.2 g.), dioxane (25 ml.) and water (25 ml.) was refluxed under heating for 15 hours with stirring. The reaction mixture was evaporated under reduced pressure, and the residue was dissolved in water (200 ml.), washed with diethyl ether twice (200 ml. and 100 ml.) and then filtered. To the filtrate was added a mixture of diethyl ether (200 ml.) and ethyl acetate (200 ml.) and the mixture was adjusted to pH 4 with 5% sulfuric acid. The organic layer was separated, washed with a saturated aqueous solution of sodium chloride (200 ml.), dried over magnesium sulfate and then evaporated under reduced pressure. The resultant product was recrystallized from ethanol (30 ml.) to give 2-[2-amino-3-(2-fluorophenoxy)-5-chlorophenyl]acetic acid (2.7 g.), mp 154° to 156° C. Thus obtained compound was dissolved in 1N aqueous sodium hydroxide (9.13 ml.) and lyophilized to give sodium 2-[2-amino-3-(2-fluorophenoxy)-5-chlorophenyl]acetate (3.15 g.). mp>250° C.

I.R. (Nujol): 3670 (sh), 3300, 1580 cm$^{-1}$.

N.M.R. (DMSO-d$_6$): (ppm) 3.40 (2H, s), 6.50–7.50 (6H, m).

EXAMPLE 30

Preparation of sodium 2-[2-amino-3-(2-chlorophenylthio)phenyl]acetate

A mixture of 2-oxo-7-(2-chlorophenylthio)indoline (5.0 g.), sodium hydroxide (1.5 g.), dioxane (15 ml.) and water (15 ml.) was refluxed for 14 hours with stirring. The reaction mixture was concentrated under reduced pressure. The residue was recrystallized from water twice and washed with diethyl ether to give crystals of the captioned compound (3.5 g.), mp 209° to 212° C.

I.R. (Nujol): 3220 (sh), 3180, 3130 (sh), 1630 cm$^{-1}$.

N.M.R. (DMSO-d$_6$): δ(ppm) 3.30 (2H, s), 6.47–7.67 (7H, m).

EXAMPLE 31

Preparation of 2-(2-amino-3-phenylsulfinylphenyl)acetic cid and its sodium salt.

A mixture of 2-oxo-7-phenylsulfinylindoline (4.3 g.), sodium hydroxide (1.2 g.), water (10 ml.) and dioxane (10 ml.) was refluxed for 6 hours with stirring. The reaction mixture was evaporated under reduced pressure, and the residue was dissolved in water and washed with diethyl ether. The aqueous solution was adjusted to pH 4 with 5% sulfuric acid and extracted with diethyl ether. The extract was washed with a saturated aqueous solution of sodium chloride twice, dried over magnesium sulfate and evaporated under reduced pressure. The residue was washed with a mixture of ethanol and diisopropyl ether to give crystals of 2-(2-amino-3-phenylsulfinylphenyl)acetic acid (1.95 g.).

I.R. (Nujol): 3400, 3320, 3230, 1700, 1640 cm$^{-1}$.

N.M.R. (DMSO-d$_6$): δ(ppm) 3.50 (2H, s), 5.73 (2H, broad s), 6.30–7.70 (8H, m).

The above product (1.95 g.) was dissolved in a solution of sodium bicarbonate (0.6 g.) in water (20 ml.) and the solution was lyophilized and then washed with ethanol to give crystals of sodium 2-(2-amino-3-phenylsulfinylphenyl)acetate (1.0 g.). mp 245° to 247° C. (dec.).

I.R. (Nujol): 3430, 3200, 1615, 1040 cm$^{-1}$.

N.M.R. (DMSO-d$_6$/D$_2$O): δ(ppm) 3.16 (2H, s), 6.40 (2H, s), 6.50–7.70 (8H, m).

EXAMPLE 32

Preparation of sodium 2-[2-amino-3-(2-chlorophenylsulfinyl)phenyl]acetate

A mixture of 2-oxo-7-(2-chlorophenylsulfinyl)indoline (5.0 g.), dioxane (30 ml.), sodium hydroxide (2.5 g.) and water (30 ml.) was refluxed for 8 hours with stirring. The reaction mixture was evaporated under reduced pressure, and the residue was dissolved in water under heating and filtered. The filtrate was adjusted to about pH 4 with 5% sulfuric acid and extracted with diethyl ether. The extract was washed with a saturated aqueous solution of sodium chloride, dried over magnesium sulfate and evaporated under reduced pressure. The residue was dissolved in 1N sodium hydroxide (14.2 ml.) under heating and the solution was evaporated to dryness under reduced pressure. The oily residue was dissolved in ethanol (20 ml.) and crystallized with diethyl ether to give crystals of the captioned compound (2.9 g.). mp 248° to 251° C. (dec.).

I.R. (Nujol): 3200, 3110, 3030, 1610, 1020 cm$^{-1}$.

N.M.R. (DMSO-d$_6$): δ(ppm) 3.20 (2H, s), 6.53–8.20 (9H, m).

EXAMPLE 33

Preparation of 2-(2-amino-3-phenylsulfonylphenyl)acetic acid and its sodium salt A mixture of 2-oxo-7-phenylsulfonylindoline (6.50 g.), dioxane (100 ml.), sodium hydroxide (3.0 g.) water (50 ml.) was refluxed under heating for 16 hours with stirring. The reaction mixture was evaporated under reduced pressure, and the residue was dissolved in water, washed with diethyl ether, adjusted to pH 4 with 1N sulfuric acid and then extracted with diethyl ether. The extract was washed with water, dried over magnesium sulfate, treated with activated charcoal and evaporated under reduced pressure. The residue was washed with a mixture of ethanol and diethyl ether and cooled. The precipitates were collected by filtration to give white crystals of 2-(2-amino-3-phenylsulfonylphenyl)acetic acid (3.60 g.). mp 218° to 220° C.

I.R. (Nujol): 3450, 3350, 3250, 1730, 1640 cm$^{-1}$.

N.M.R. (DMSO-d$_6$): δ(ppm) 3.56 (2H, s), 6.0 (2H, broad s), 6.60–8.06 (8H, m).

Thus obtained compound (3.40 g.) was dissolved in 1N sodium hydroxide (11.6 ml.) and the solution was evaporated under reduced pressure. The residue was recrystallized from aqueous ethanol to give white crystals of sodium 2-(2-amino-3-phenylsulfonylphenyl)acetate (1.40 g.). mp 250° C. (dec.).

I.R. (Nujol): 3380, 3180 (broad), 1630, 1140 cm$^{-1}$.

N.M.R. (D$_2$O): δ(ppm) 3.43 (2H, s), 6.90–8.10 (8H, m).

EXAMPLE 34

Preparation of sodium 2-(2-amino-3-anilinophenyl)acetate

A mixture of 2-oxo-7-anilinoindoline (3 g.), sodium hydroxide (1.07 g.), dioxane (10 ml.) and water (50 ml.) was refluxed under heating for 22 hours with stirring. After cooling, the reaction mixture was filtered, and the filtrate was evaporated under reduced pressure. The residue was dissolved in ethanol under heating and filtered. The filtrate was evaporated under reduced pressure and the oily residue was crystallized with ethyl acetate, collected by filtration, washed with ethyl acetate and dried to give powdery crystals of the captioned compound (1.8 g.). mp 195° to 200° C.

I.R. (Nujol): 3370, 1570 cm$^{-1}$.

N.M.R. (DMSO-d$_6$): δ(ppm) 3.27 (2H, s), 5.20 (2H, broad s), 6.36–7.27 (8H, m), 7.20 (1H, s).

EXAMPLE 35

Preparation of 2-[2-amino-3-(2-chloroanilino)phenyl]acetic acid and its sodium salt A mixture of 2-oxo-7-(2-chloroanilino)indoline (5 g.), sodium hydroxide (1.25 g.), dioxane (30 ml.) and water (60 ml.) was refluxed under heating for 53 hours with stirring. After cooling, the reaction mixture was filtered and the filtrate was evaporated under reduced pressure. The residue was dissolved in water (50 ml.), washed with ethyl acetate, adjusted to pH 4 to 5 with 5% sulfuric acid and then extracted with ethyl acetate (150 ml.).

The extract was evaporated under reduced pressure and the residue was subjected to column chromatography on silica gel (60 g.) and eluted with ethyl acetate to give 2-[2-amino-3-(2-chloroanilino)phenyl]acetic acid (2.4 g.). mp 230° to 232° C.

Thus obtained compound was dissolved in a solution of sodium hydroxide (35 mg.) in water (50 ml.) and filtered. The filtrate was lyophilized to give sodium 2-[2-amino-3-(2-chloroanilino)phenyl]acetate (2.5 g.).

I.R. (Nujol): 3400, 1590, 1570 cm$^{-1}$.

N.M.R. (DMSO-d$_6$): δ(ppm) 3.25 (2H, s), 5.23 (2H, broad s), 6.45-7.40 (7H, m).

EXAMPLE 36

Preparation of 2-[2-amino-3-(4-chloroanilino)phenyl]acetic acid and its sodium salt A mixture of 2-oxo-7-(4-chloroanilino)indoline (3.2 g.), sodium hydroxide (1.2 g.), dioxane (20 ml.) and water (40 ml.) was refluxed under heating for 118 hours with stirring. After cooling, the reaction mixture was filtered and the filtrate was evaporated under reduced pressure. The residue was dissolved in water and washed with ethyl acetate, adjusted to pH 2 to 3 with 5% sulfuric acid and extracted with ethyl acetate. The extract was washed with water, dried over magnesium sulfate and concentrated under reduced pressure. The residue was washed with benzene to give 2-[2-amino-3-(4-chloroanilino)phenyl]acetic acid (2.7 g.). mp 190° to 192° C.

Thus obtained compound (2.6 g.) was dissolved in a solution of sodium hydroxide (376 mg.) in water (50 ml.) and filtered. The filtrate was lyophilized to give sodium 2-[2-amino-3-(4-chloroanilino)phenyl]acetate (2.8 g.).

I.R. (Nujol): 3350, 1590 cm$^{-1}$.

N.M.R. (DMSO-d$_6$): (ppm) 3.33 (2H, s), 5.40 (2H, s), 6.40-7.33 (7H, m), 7.52 (1H, s).

EXAMPLE 37

(1) Preparation of ethyl 2-(2-acetamido-3-phenoxyphenyl)acetate

A solution of acetyl chloride (1.38 g.) in methylene chloride (10 ml.) was added to a mixture of ethyl 2-(2-amino-3-phenoxyphenyl)acetate (4.3 g.), pyridine (1.9 g.) and dried methylene chloride (50 ml.) over 10 minutes at 5° C. with stirring and stirred for 30 minutes at the same temperature. The reaction mixture was concentrated under reduced pressure and to the residue was added 10% hydrochloric acid. The mixture was extracted with ethyl acetate, and the extract was washed with water, dried over magnesium sulfate and then evaporated. The residue was crystallized with a mixture of benzene and n-hexane to give the captioned compound (3.65 g.). mp 106° to 107° C.

I.R. (Nujol): 3200, 1730, 1660 cm$^{-1}$.

N.M.R. (DMSO-d$_6$): δ(ppm) 1.15 (3H, t, J=8 Hz), 1.82 (3H, s), 3.59 (2H, s), 4.03 (2H, q, J=8 Hz), 6.80-7.40 (8H, m), 9.28 (1H, s).

(2) Preparation of 2-(2-acetamido-3-phenoxyphenyl)acetic acid

A mixture of ethyl 2-(2-acetamido-3-phenoxyphenyl)acetate (3.65 g.), potassium hydroxide (1.3 g.) and methanol (50 ml.) was stirred for 4 hours at ambient temperature and then for an hour at 40° C. Methanol was distilled off from the reaction mixture under reduced pressure and the residue was dissolved in water. The solution was washed with diethyl ether, adjusted to pH 1.0 with 5% sulfuric acid and extracted with ethyl acetate. The extract was washed with water, dried over magnesium sulfate and then evaporated. The residue was recrystallized from a mixture of ethanol and n-hexane to give white needles of the captioned compound (3.1 g.). mp 155° to 156° C. Thus obtained product was dissolved in an aqueous solution of sodium bicarbonate and the solution was adjusted to pH 1.0 with 10% hydrochloric acid. The precipitates were collected by filtration and dried to give the pure compound (2.5 g.), mp 155° to 156° C.

I.R. (Nujol): 3400, 3200, 1720, 1680, 1650 cm$^{-1}$.

N.M.R. (DMSO-d$_6$): δ(ppm) 1.85 (3H, s), 3.58 (2H, s), 6.78-7.55 (8H, m), 9.37 (1H, broad s).

EXAMPLE 38

(1) A mixture of 2-oxo-3-methylthio-7-(2-methoxyphenoxy)indoline (3.9 g) and Raney nickel (3.9 ml) in dried ethanol (70 ml) was treated in a similar manner to that of Preparation 15-(2) to give 2-oxo-7-(2-methoxyphenoxy)indoline (0.7 g), mp 145°-147° C.

I.R. (NaCl, Nujol): 3100, 3050, 1715, 1640, 1600, 1500, 1470, 1410, 1260, 1210 cm$^{-1}$.

N.M.R. (DMSO-d$_6$): δ (ppm) 3.57 (2H, s), 3.80 (3H, s), 6.37-7.33 (7H, m), 10.63 (1H, broad s).

Analysis for C$_{15}$H$_{13}$NO$_3$: Calculated: C 70.58, H 5.13, N 5.49; Found: C 71.08, H 4.92, N 5.44.

(2) A mixture of 2-oxo-7-(2-methoxyphenoxy)indoline (2.7 g) and sodium hydroxide (2.1 g) in water (30 ml) and dioxane (30 ml) was refluxed with stirring for 30 hrs. The reaction mixture was concentrated in vacuo, and the residue was dissolved in water and filtered. The filtrate was washed with diethyl ether, neutralized with 5% sulfuric acid and extracted with diethyl ether. The extract was washed with saline, dried over magnesium sulfate and then evaporated in vacuo. The residue was treated with an aqueous solution of sodium bicarbonate, and the resultant oily substance (3.0 g) was crystallized by treating with ethyl acetate to give crystalline sodium 2-[2-amino-3-(2-methoxyphenoxy)phenyl]acetate (1.55 g). mp 101°-103° C. I.R. (NaCl, Nujol): 3500, 3400, 1615, 1600, 1580, 1500, 1470, 1390, 1310, 1265, 1200 cm$^{-1}$.

N.M.R. (DMSO-d$_6$): δ (ppm) 3.23 (2H, s), 3.80 (3H, s), 5.50 (2H, broad s), 6.40-7.26 (7H, m).

EXAMPLE 39

(1) A mixture of 2-oxo-3-methylthio-7-(α-naphthoxy)indoline (5.4 g) and Raney nickel (12 ml) in dioxane (70 ml) was stirred at 50° C. for 1.5 hrs. The reaction mixture was allowed to stand and the supernatant was separated by decantation. To the residue was added dioxane and the supernatant was separated again. The dioxane solutions were combined and filtered. The filtrate was evaporated in vacuo, and the oily residue (5.2 g) was crystallized by treating with ethanol to give 2-oxo-7-(α-naphtoxy)indoline (3.15 g). mp 158°-160° C.

I.R. (NaCl, Nujol): 3300, 3200, 1680, 1470, 1200 cm$^{-1}$.

N.M.R. (DMSO-d$_6$): δ (ppm) 3.63 (2H, s), 6.70-8.33 (10H, m), 10.80 (1H, s).

Analysis for C$_{18}$H$_{13}$NO$_2$: Calculated: C 78.53, H 4.76, N 5.08; Found: C 78.43, H 4.61, N 4.96.

(2) A mixture of 2-oxo-7-(α-naphthoxy)indoline (3.1 g) and sodium hydroxide (1 g), in dioxane (30 ml) and water (60 ml) was refluxed with stirring for 24 hrs. After cooling the reaction mixture was filtered, and the filtrate was evaporated in vacuo.

The residue was dissolved in water and the aqueous solution was washed with ethyl acetate, adjusted to pH 2-3 with dil. sulfuric acid and then extracted with ethyl acetate. The extract was washed with water, dried over magnesium sulfate and evaporated in vacuo. The residue was crystallized by treating with benzene to give 2-[2-amino-3-(α-napthoxy)phenyl]acetic acid (1 g). mp 129°-130° C. (dec.).

This substance was dissolved in an aqueous solution of sodium hydroxide (30 ml) and filtered. The filtrate was lyophilized to give sodium 2-[2-amino-3-(α-naphthoxy)phenyl]acetate (1 g).

I.R. (NaCl, Nujol): 3360, 1570, 1470, 1380, 1270, 1240, 775 cm$^{-1}$.

N.M.R. (DMSO-d$_6$): δ (ppm) 3.33 (2H, s), 5.44 (2H, broad s), 6.35-8.38 (10H, m).

Analysis for $C_{18}H_{15}NO_3$ (free acid): Calculated: C 73.31, H 5.15, N 4.78; Found: C 73.57, H 4.85, N 4.65.

EXAMPLE 40

(1) A mixture of 2-oxo-3-methylthio-7-(β-naphthoxy)indoline (7.6 g) and Raney nickel (17 ml) in dioxane (100 ml) was treated in a similar manner to that of Example 39-(1) to give 2-oxo-7-(β-naphthoxy)indoline (5.4 g). mp 195°-197° C.

I.R. (NaCl, Nujol): 1690, 1640, 1470, 1250, 1220 cm$^{-1}$.

N.M.R. (DMSO-d$_6$): δ (ppm) 3.67 (2H, s), 6.93-8.08 (10H, m), 10.70 (1H, s).

Analysis for $C_{18}H_{13}NO_2$: Calculated: C 78.53, H 4.76, N 5.09; Found: C 78.45, H 4.48, N 4.97.

(2) A mixture of 2-oxo-7-(β-naphthoxy)indoline (5 g) and sodium hydroxide (1.6 g) in dioxane (40 ml) and water (80 ml) was refluxed with stirring for 72 hrs. After cooling, the reaction mixture was filtered, and the filtrate was evaporated in vacuo. The residue was dissolved in hot ethanol and filtered. The filtrate was evaporated in vacuo, and ethyl acetate was added to the residue. The resultant ethyl acetate solution was heated. The precipitating crystals were collected by filtration and recrystallized from ethanol to give 2-[2-amino-3-(β-naphthoxy)phenyl]acetic acid (2.9 g). This substance was dissolved in an aqueous sodium bicarbonate, and the solution was filtered and lyophilized to give sodium 2-[2-amino-3-(β-naphtoxy)phenyl]acetate (2.8 g).

I.R. (NaCl, Nujol): 3400, 1570, 1460, 1380, 1250, 1220, 1170, 750 cm$^{-1}$.

N.M.R. (DMSO-d$_6$): δ(ppm) 3.37 (2H, s), 5.42 (2H, broad s), 6.43-8.00 (10H, m).

EXAMPLE 41

(1) A mixture of ethyl 2-[2-amino-3-(2-chlorophenoxy)phenyl]acetate (11.8 g), methyl iodide (11.9 g) and potassium carbonate (10.7 g) in dried dimethylformamide (100 ml) was stirred at room temperature for 17 hrs. The reaction mixture was poured into water (400 ml) and extracted with diethyl ether (150 ml×2). The extract was washed with saline, dried over magnesium sulfate and evaporated in vacuo. The oily residue (12.7 g) was subjected to column chromatography on silica gel and eluted with a mixture of benzene and n-hexane (1:1) to give oily ethyl 2-[2-dimethylamino-3-(2-chlorophenoxy)phenyl]acetate (7.4 g).

I.R. (liquid film): 1730, 1570, 1255, 1160 cm$^{-1}$.

N.M.R. (CCl$_4$): δ(ppm) 1.28 (3H, t, J=7 Hz) 2,75 (6H, s), 3.64 (2H, s), 4.10 (2H, q, J=7 Hz), 6.50-7.48 (7H, m).

(2) A solution of ethyl 2-[2-dimethylamino-3-(2-chlorophenoxy)phenyl]acetate (7.4 g) in methanol (50 ml) was added to a solution of potassium hydroxide (6.2 g) in methanol (50 ml), and the mixture was refluxed with stirring for an hour. The reaction mixture was evaporated in vacuo, and the residue was dissolved in water. The aqueous solution was adjusted to pH 7.0 with conc.hydrochloric acid and extracted twice with diethyl ether. The extract was washed with saline, dried over magnesium sulfate and evaporated in vacuo to give oily residue (6.8 g). The oil was crystallized by treating with 5% hydrochloric acid to give 2-[2-dimethylamino-3-(2-chlorophenoxy)phenyl]acetic acid hydrochloride (5.5 g). mp 181°-183° C.

I.R. (NaCl, Nujol): 3400, 3370 (sh), 2700, 1720, 1480, 1275, 1195 cm$^{-1}$.

N.M.R. (DMSO-d$_6$): δ(ppm) 3.13 (6H, s), 4.03 (2H, s), 6.57-7.90 (7H, m).

Analysis for $C_{16}H_{17}NO_3Cl_2 \cdot H_2O$: Calculated: C 53.35, H 5.31, N 3.88, Cl 19.68, H$_2$O 5.00; Found: C 53.45, H 5.26, N 3.91, Cl 19.45, H$_2$O 5.04.

EXAMPLE 42

A solution of ethyl 2-[2-nitro-3-(2-fluorophenoxy)phenyl]acetate in methanol (50 ml) was added to a solution of potassium hydroxide (20 g) in methanol (50 ml) with stirring under ice-cooling, and the mixture was stirred at room temperature for 30 minutes. Water (700 ml) was added to the reaction mixture and the resultant aqueous solution was adjusted to pH 2.0 with conc. hydrochloric acid. The precipitating crystals were collected by filtration, washed with water and recrystallized from a mixture of ethyl acetate and n-hexane (1:1) to give 2-[2-nitro-3-(2-fluorophenoxy)phenyl]acetic acid (31.9 g). mp 144°-146° C.

I.R. (NaCl, Nujol): 1710, 1590, 1530, 1500, 1460, 1280 cm$^{-1}$.

N.M.R. (DMSO-d$_6$): δ(ppm) 3.80 (2H, s) 6.85-7.80 (7H, m).

EXAMPLE 43

(1) A solution of mesyl chloride (0.95 g) in pyridine (3 ml) was added to a solution of ethyl 2-[2-amino-3-(2-chlorophenoxy)phenyl]acetate (2.3 g) in pyridine (10 ml), and the mixture was stirred for an hour. The reaction mixture was poured into water (100 ml) and extracted with diethyl ether (80 ml×2). The extract was washed with 5% hydrochloric acid (50 ml×2) and saline, dried over magnesium sulfate and then evaporated in vacuo. The oily residue (2.5 g) was crystallized by treating with ethanol and the resultant solid substance was recrystallized from ethanol to give ethyl 2-[2-mesylamino-3-(2-chlorophenoxy)phenyl]acetate (0.7 g). mp 145°-149° C.

I.R. (NaCl, Nujol): 3300, 1730, 1580, 1470, 1340, 1210 cm$^{-1}$.

N.M.R. (DMSO-d$_6$): δ(ppm): 1.23 (3H, t, J=7 Hz), 3.13 (3H, s), 3.92 (2H, s), 4.13 (2H, q, J=7 Hz), 6.53-7.80 (7H, m), 9.20 (1H, s).

(2) Ethyl 2-[2-mesylamino-3-(2-chlorophenoxy)phenyl]-acetate (0.8 g) was dissolved in 1N-sodium hydroxide (10 ml) by heating, and the solution was allowed to stand at room temperature for 10 minutes. To the reaction mixture was added water (20 ml), and the mixture was washed with diethyl ether. The aqueous solution was adjusted to pH 2 with conc. hydrochloric acid. The precipitating crystals were collected by filtration, washed with water and recrystallized from benzene to give 2-[2-mesylamino-3-(2-chlorophenoxy)-phenyl]acetic acid (0.58 g). mp 159°–163° C.

I.R. (NaCl, Nujol): 3300, 1730, 1580, 1480, 1470, 1330, 1250 cm$^{-1}$.

N.M.R. (DMSO-d$_6$): δ(ppm): 3.10 (3H, s), 3.83 (2H, s), 6.50–7.77 (7H, m).

Analysis for C$_{15}$H$_{14}$NO$_5$SCl: Calculated: C 50.64, H 3.97, N 3.94, S 9.01, Cl 9.97; Found: C 50.94, H 3.93, N 3.84, S 9.07, Cl 10.15.

EXAMPLE 44

(1) A mixture of iron powder (21.6 g) and ammonium chloride (2.2 g) in ethanol (200 ml) and water (75 ml) and ethyl 2-[2-nitro-3-(4-chlorophenylthio)phenyl]acetate (21.6 g) were treated in a similar manner to that of Preparation 28-(1) to give 2-oxo-7-(4-chlorophenylthio)indoline (14.9 g). mp 186°–188° C.

I.R. (NaCl, Nujol): 3100, 3030, 1710, 1610, 1325, 1220, 1090 cm$^{-1}$.

N.M.R. (CDCl$_3$):

δ(ppm): 3.60 (2H, s), 6.87–7.57 (7H, m), 8.17 (1H, broad s).

(2) A solution of 2-oxo-7-(4-chlorophenylthio)indoline (7.0 g) in chloroform (400 ml) and m-chloroperbenzoic acid (5.15 g) were treated in a similar manner to that of Preparation 28-(2) to give 2-oxo-7-(4-chlorophenylsulfinyl)indoline (3.85 g). mp 191°–194° C.

I.R. (NaCl, Nujol): 3100, 3075, 3050, 1710, 1455, 1215, 1050 cm$^{-1}$.

N.M.R. (CDCl$_3$): δ(ppm): 3.40 (2H, s), 6.90–7.68 (7H, m).

Analysis for C$_{14}$H$_{10}$NO$_2$SCl Calculated: C 57.63, H 3.45, N 4.80, S 10.99 Cl 12.15; Found: C 57.41, H 3.40, N 4.58, S 10.97, Cl 12.05.

(3) A mixture of 2-oxo-7-(4-chlorophenylsulfinyl)indoline (4.7 g) and dioxane (30 ml) was added to a solution of sodium hydroxide (2.5 g) in water (30 ml), and the mixture was refluxed with stirring for 15 hrs. Dioxane was distilled off from the reaction mixture in vacuo, and the residue was dissolved in water and washed with diethyl ether. The aqueous solution was adjusted to pH 7 with 5% sulfuric acid and extracted with ethyl acetate (200 ml×2). The extract was washed with saline, dried over magnesium sulfate and then evaporated in vacuo. The residue was dissolved in 1N-sodium hydroxide (12.2 ml) under heating and the solution was concentrated in vacuo. The residue was recrystallized from ethanol twice to give powdery sodium 2-[2-amino-3-(4-chlorophenylsulfinyl)phenyl]acetate (1.5 g). mp 242°–245° C. (dec.).

I.R. (NaCl, Nujol): 3440, 3360, 3250, 1650, 1570, 1470, 1390, 1280 cm$^{-1}$.

N.M.R. (D$_2$O): δ(ppm) 3.40 (2H, s), 6.72–7.70 (7H, m).

EXAMPLE 45

(1) m-Chloroperbenzoic acid (purity 85%, 14.3 g) was added portionwise to a solution of 2-oxo-7-(4-chlorophenylthio)indoline (7.75 g) in chloroform (400 ml) with stirring. The mixture was stirred at room temperature for 3 hrs. and then allowed to stand for 2 days. The reaction mixture was washed with saturated aqueous sodium bicarbonate and water, dried over magnesium sulfate and then evaporated in vacuo. The crystalline residue was recrystallized from dioxane (20 ml) to give 2-oxo-7-(4-chlorophenylsulfonyl)indoline (3.8 g). mp 218°–221° C.

I.R. (NaCl, Nujol): 3440, 3300, 3070, 1700, 1460, 1255, 1140 cm$^{-1}$.

N.M.R. (DMSO-d$_6$): δ(ppm) 3.56 (2H, s), 7.00–8.08 (7H, m).

Analysis for C$_{14}$H$_{10}$NO$_3$SCl: Calculated: C 54.64, H 3.28, N 4.55, S 10.42, Cl 11.52; Found: C 54.35, H 3.21, N 4.52, S 10.39, Cl 11.58.

(2) A mixture of 2-oxo-7-(4-chlorophenylsulfonyl)indoline (3.3 g) and dioxane (20 ml) was added to a solution of sodium hydroxide (2.0 g) in water (20 ml), and the mixture was refluxed with stirring for 6 hrs. The reaction mixture was concentrated in vacuo, and the residue was dissolved in water. The aqueous solution was washed with diethyl ether, adjusted to pH 4 with 5% sulfuric acid and extracted with diethyl ether. The extract was washed with saline, dried over magnesium sulfate, treated with charcoal and then evaporated in vacuo to give 2-[2-amino-3-(4-chlorophenylsulfonyl)phenyl]acetic acid (2.8 g). mp 139°–141° C.

I.R. (NaCl, Nujol): 3470, 3390, 1710, 1310, 1140, 1090 cm$^{-1}$.

N.M.R. (CDCl$_3$): δ(ppm) 3.53 (2H, s), 6.60–8.03 (9H, m).

Thus obtained free acid (2.8 g) was dissolved in 1N-sodium hydroxide (8.6 ml) under heating, and the solution was concentrated in vacuo. The residue was recrystallized from a mixture of ethanol and methanol to give sodium 2-[2-amino-3-(4-chlorophenylsulfonyl)phenyl]acetate (1.7 g). mp 262°–265° C. (dec.).

I.R. (NaCl, Nujol): 3520, 3430, 1635, 1610 cm$^{-1}$.

N.M.R. (DMSO-d$_6$): δ(ppm) 3.23 (2H, s), 6.53–8.16 (9H, m).

EXAMPLE 46

(1) Chlorine gas (2.92 g), ethyl methylthioacetate (5.5 g), 2-chloro-5-phenoxyaniline (18 g), triethylamine (6.24 g) and methylene chloride (100 ml) were treated in a similar manner to that of Preparation 15-(1). The resultant oily residue was dissolved in water, and to the aqueous solution was added conc. hydrochloric acid. After warming, the aqueous layer was removed by decantation. The oily residue was dissolved in ethyl acetate, and the solution was washed with saturated aqueous sodium bicarbonate and saline, dried over magnesium sulfate and then evaporated in vacuo. The residue was allowed to stand at room temperature for 2 days, and the precipitates were washed with diethyl ether (50 ml) to give 2-oxo-3-methylthio-4-phenoxy-7-chloroindoline (3.8 g). Th same product (2.4 g) was obtained from the washings. Total yield 6.2 g. mp. 127°–128° C.

I.R. (NaCl, Nujol): 3170, 3070, 1710, 1260 cm$^{-1}$.

N.M.R. (DMSO-d$_6$): (ppm) 2.02 (3H, s), 4.44 (1H, s), 6.43–7.47 (7H, m), 11.07 (1H, s).

Analysis for C$_{15}$H$_{12}$NO$_2$SCl: Calculated: C 58.92, H 3.96, N 4.58; Found: C 58.99, H 3.84, N 4.80.

(2) 2-Oxo-3-methylthio-4-phenoxy-7-chloroindoline (6 g) was added to a mixture of Raney nickel (15 ml) and dioxane (80 ml), and the mixture was stirred at 70° C. for 2 hours. The reaction mixture was allowed to stand at room temperature, and the supernatant was separated by decantation. To the residue was added dioxane (50 ml), and the supernatant was separated again. The dioxane solution was combined and filtered. The filtrate was evaporated in vacuo, and the residue was washed with diethyl ether and dried to give 2-oxo-4-phenoxy-7-chloroindoline (4.3 g). mp. 200°–202° C.

I.R. (NaCl, Nujol): 3125, 3060, 1710, 1260 cm$^{-1}$.

N.M.R. δ(ppm) 3.49, (2H, s), 6.49–7.60 (7H, m), 10.92 (1H, broad s).

(3) A mixture of 2-oxo-4-phenoxy-7-chloroindoline (4.2 g) and sodium hydroxide (1.3 g) in water (40 ml) and dioxane (10 ml) was refluxed for 24 hrs. After cooling, the reaction mixture was filtered, and the filtrate was evaporated in vacuo. The residue was dissolved in ethanol under heating, and the solution was filtered. The filtrate was allowed to stand under ice-cooling, and the precipitating crystals were collected by filtration, washed with ethanol and dried to give sodium 2-(2-amino-3-chloro-6-phenoxyphenyl)acetate (1.8 g). The same product (2.3 g) was obtained from the mother liquid. Total yield 4.1 g. mp>240° C.

I.R. (NaCl, Nujol): 3430, 3350, 1550, 1230 cm$^{-1}$.

N.M.R. (DMSO-d$_6$): δ(ppm) 3.43 (2H, s), 5.84 (2H, broad s), 6.10–7.53 (7H, m).

Analysis for $C_{14}H_{11}NO_3ClNa.2/3H_2O$: Calculated: C 53.94, H 3.98, N 4.49, Cl 11.38, H$_2$O 3.84; Found: C 53.65, H 3.81, N 4.49, Cl 10.94, H$_2$O 3.67.

EXAMPLE 47

A solution of potassium hydroxide (3 g) in methanol (30 ml) was added to a solution of ethyl 2-[2-nitro-3-(o-tolyloxy)phenyl]acetate (3.9 g) in methanol (30 ml), and the mixture was stirred at room temperature for an hour. The reaction mixture was evaporated in vacuo, and the residue was dissolved in water. The aqueous solution was washed with diethyl ether and acidified with conc. hydrochloric acid. The precipitating crystals were collected by filtration and recrystallized from ethanol to give 2-[2-nitro-3-(o-tolyloxy)phenyl]acetic acid (1.5 g). mp 158°–160° C.

I.R. (NaCl, Nujol): 2750, 2670, 2560, 1730, 1615, 1520, 1455, 1285 cm$^{-1}$.

N.M.R.: δ(ppm) 2.20 (3H, s), 3.77 (2H, s), 6.70–7.65 (7H, m).

Analysis for $C_{15}H_{13}NO_5$: Calculated: C 62.71, H 4.56, N 4.88; Found: C 62.81, H 4.49, N 4.99.

EXAMPLE 48

(1) A mixture of ethyl 2-[2-nitro-3-(2-chlorophenoxy)phenyl]acetate and sodium hydroxide in water was treated in a similar manner to that of Example 5-(2) to give sodium 2-[2-nitro-3-(2-chlorophenoxy)phenyl]acetate.

(2) Thus obtained sodium 2-[2-nitro-3-(2-chlorophenoxy)phenyl]acetate was subjected successively to catalytic reduction using Raney nickel to give sodium 2-[2-amino-3-(2-chlorophenoxy)phenyl]acetate. This product was identified with crop obtained in Example 5-(2) by I.R. and N.M.R. spectra.

EXAMPLE 49

(1) A mixture of iron powder and ammonium chloride in ethanol and water and ethyl 2-[2-nitro-3-(2-chlorophenoxy)phenyl]acetate were treated in a similar manner to that of Preparation 28-(1) to give 2-oxo-7-(2-chlorophenoxy)indoline (2) Thus obtained 2-oxo-7-(2-chlorophenoxy)indoline was treated successively with sodium hydroxide in a similar manner to that of Example 29 to give sodium 2-[2-amino-3-(2-chlorophenoxy)phenyl]acetate, which was identified with the crop obtained in Example 5-(2) by I.R. and N.M.R. spectra.

EXAMPLE 50

(1) 2-(2-Chlorophenoxy)aniline, chlorine gas, ethyl 2-methylthioacetate, triethylamine and methylene chloride were treated in a similar manner to that of Preparation 15-(1) to give 2-oxo-3-methylthio-7-(2-chlorophenoxy)indoline.

(2) A mixture of thus obtained 2-oxo-3-methylthio-7-(2-chlorophenoxy)indoline and Raney nickel in dioxane was treated in a similar manner to that of Preparation 15-(2) to give 2-oxo-7-(2-chlorophenoxy)indoline.

(3) Thus obtained 2-oxo-7-(2-chlorophenoxy)indoline was treated successively with sodium hydroxide in a similar manner to that of Example 29 to give sodium 2-[2-amino-3-(2-chlorophenoxy)phenyl]acetate, which was identified with the crop obtained in Example 5-(2) by I.R. and N.M.R. spectra.

EXAMPLE 51

(1) A mixture of 2-nitro-3-chlorobenzoic acid (45.2 g), o-chlorophenol (57.6 g), sodium hydroxide (17.9 g) and copper powder (4.5 g) was stirred vigorously at 160°–180° C. for 55 minutes. The hot reaction mixture was poured into water, and the mixture was stirred and filtered. The filtrate was adjusted to pH 1 with hydrochloric acid and extracted with ethyl acetate (300 ml+200 ml). To the extract was added water (300 ml), and the mixture was adjusted to pH 8 and extracted with water. The aqueous extract was adjusted to pH 1 with hydrochloric acid and extracted again with ethyl acetate. The extract was dried over magnesium sulfate, treated with activated charcoal and then evaporated in vacuo.

To the oily residue (74.3 g) were added ethanol (500 ml) and 30% HCl-ethanol (20 ml), and the mixture was refluxed with stirring for 8 hrs. After evaporation, the residue was dissolved in ethyl acetate, and the solution was washed with water, aqueous sodium bicarbonate and water in turn, dried over magnesium sulfate, treated with activated charcoal and then evaporated in vacuo. To the oily residue (50 g) was added methylene chloride and the mixture was filtered. The filtrate was subjected to column chromatography on silica gel (500 g) and eluted with a mixture of methylene chloride and n-hexane (1:3). The eluate was evaporated in vacuo, and the residue was washed with isopropyl alcohol-hexane and dried in vacuo to give ethyl 2-nitro-3-(2-chlorophenoxy)benzoate (16.3 g).

(2) Ethyl 2-nitro-3-(2-chlorophenoxy)benzoate was suspended in 1N-potassium hydroxide (60 ml) and ethanol (60 ml) and stirred for 1.7 hrs. Ethanol was distilled off from the reaction mixture, and the remaining aqueous solution was washed with diethyl ether and acidified at 0° C. The precipitating crystals were collected by filtration, washed with water and dried over phosphorus pentoxide in vacuo to give 2-nitro-3-(2-chlorophenoxy)benzoic acid (11.3 g). mp 185°–187° C.

(3) Sodium borohydride (4.4 g) and boron trifluoridediethyl ether (23.7 ml) were added to a solution of 2-nitro-3-(2-chlorophenoxy)benzoic acid (11.3 g) in dried tetrahydrofuran (100 ml), and the mixture was stirred for 3 hrs. at room temperature. To the reaction mixture were added ethyl acetate (200 ml) and water (200 ml), and the mixture was filtered. The ethyl acetate layer was separated from the filtrate, washed with aqueous sodium bicarbonate and saline, dried and then evaporated in vacuo. The oily residue (15.1 g) was subjected to column chromatography on silica gel (150 g) and eluted with methylene chloride to give 2-nitro-3-(2-chlorophenoxy)benzyl alcohol (10.5 g).

(4) A solution of Phosphorus tribromide (1.72 ml) in methylene chloride (15 ml) was added dropwise to a solution of 2-nitro-3-(2-chlorophenoxy)benzyl alcohol (9.6 g) in methylene chloride (80 ml) at $-10°$ C., and the mixture was stirred at $0°$ C. for an hour. To the reaction mixture was added water (50 ml), and the methylene chloride layer was separated, washed with aqueous sodium bicarbonate and saline, dried and then evaporated in vacuo. The oily residue was subjected to column chromatography on silica gel (110 g) and eluted with a mixture of n-hexane and benzene (2:1). The eluate was evaporated in vacuo, and the residue was recrystallized from a mixture of benzene and n-hexane to give 2-nitro-3-(2-chlorophenoxy)benzyl bromide (2.7 g). mp $68°-70°$ C.

I.R. (Nujol): 1610, 1580, 1530, 1450 cm$^{-1}$.

N.M.R. (DMSO-d$_6$): δ(ppm) 4.73 (2H, s), 6.8–7.1 (1H, m), 7.1–7.8 (6H, m).

(5) 2-Nitro-3-(2-chlorophenoxy)benzyl bromide (100 mg) and ethanol (3 ml) were added to a solution of potassium cyanide (24.3 mg) in water (1 ml), and the mixture was stirred at $55°-60°$ C. for 1.5 hrs.

To the reaction mixture was added water (5 ml), and the mixture was extracted with ethyl acetate (7 ml×2). The extract was washed with saline (3 ml), dried over magnesium sulfate, filtered and then evaporated in vacuo to give oily 2-[2-nitro-3-(2-chlorophenoxy)-phenyl]acetonitrile (82.1 mg).

(6) 2-[2-Nitro-3-(2-chlorophenoxy)phenyl]acetonitrile obtained above was dissolved in dried ethanol containing dry hydrochloric acid. The resulting solution was allowed to stand at $2°$ C. for 16 hrs. To the reaction mixture was added water (5 ml) and ethyl acetate (10 ml). The solution was heated for 5 minutes at $50°$ C. The organic layer and water were separated. The ethyl acetate layer was washed with water (5 ml), saturated aqueous sodium bicarbonate (4 ml), and water (4 ml). The aqueous washings were extracted with ethyl acetate. The ethyl acetate layers were combined, dried over magnesium sulfate and evaporated in vacuo to give oily ethyl 2-[2-nitro-3-(2-chlorophenoxy)phenyl]acetate.

(7) Thus obtained ethyl 2-[2-nitro-3-(2-chlorophenoxy)phenyl]acetate was treated in a similar manner to those of Examples 5-(1) and 5-(2) to give sodium 2-[2-amino-3-(2-chlorophenoxy)phenyl]acetate.

We claim:

1. A compound having antiflammatory, analgesic and antipyretic properties of the formula:

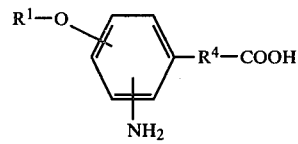

wherein $R^1$ is phenyl substituted with halogen; $R^4$ is a group of the formula $C_nH_{2n}$ in which n is an integer of 1 to 7; or a pharmaceutically acceptable salt thereof.

2. The compound of claim 1, wherein said compound is 2-[2-amino-3-(2-chlorophenoxy)phenyl] acetic acid or its alkali metal salt.

* * * * *